(12) United States Patent
Robinson et al.

(10) Patent No.: US 9,597,024 B2
(45) Date of Patent: Mar. 21, 2017

(54) METHODS AND APPARATUSES FOR NONINVASIVE DETERMINATIONS OF ANALYTES

(71) Applicants: M Ries Robinson, Albuquerque, NM (US); Russell E Abbink, Sandia Park, MN (US); Robert D Johnson, Federal Way, WA (US)

(72) Inventors: M Ries Robinson, Albuquerque, NM (US); Russell E Abbink, Sandia Park, MN (US); Robert D Johnson, Federal Way, WA (US)

(73) Assignee: Medici Instruments LLC, Albuquerque, NM (US)

( * ) Notice: Subject to any disclaimer, the term of this patent is extended or adjusted under 35 U.S.C. 154(b) by 0 days.

(21) Appl. No.: 14/250,125

(22) Filed: Apr. 10, 2014

(65) Prior Publication Data
US 2014/0303463 A1    Oct. 9, 2014

Related U.S. Application Data

(63) Continuation-in-part of application No. 13/036,012, filed on Feb. 28, 2011, now abandoned, which is a
(Continued)

(51) Int. Cl.
*G01J 4/00*    (2006.01)
*A61B 5/1455*    (2006.01)
(Continued)

(52) U.S. Cl.
CPC ........ *A61B 5/14552* (2013.01); *A61B 5/0075* (2013.01); *A61B 5/14532* (2013.01);
(Continued)

(58) Field of Classification Search
CPC ...................................................... G01J 4/00
(Continued)

(56) References Cited

U.S. PATENT DOCUMENTS 5,553,616 A * 9/1996 Ham .................. A61B 5/14558
128/925
5,687,721 A * 11/1997 Kuhls ...................... G01N 21/21
356/364

(Continued)

*Primary Examiner* — Roy M Punnoose
(74) *Attorney, Agent, or Firm* — V. Gerald Grafe

(57) ABSTRACT

The present invention provides methods and apparatuses for accurate noninvasive determination of tissue properties. Some embodiments of the present invention comprise an optical sampler having an illumination subsystem, adapted to communicate light having a first polarization to a tissue surface; a collection subsystem, adapted to collect light having a second polarization communicated from the tissue after interaction with the tissue; wherein the first polarization is different from the second polarization. The difference in the polarizations can discourage collection of light specularly reflected from the tissue surface, and can encourage preferential collection of light that has interacted with a desired depth of penetration or path length distribution in the tissue. The different polarizations can, as examples, be linear polarizations with an angle between, or elliptical polarizations of different handedness.

28 Claims, 26 Drawing Sheets

Related U.S. Application Data continuation-in-part of application No. 11/350,916, filed on Feb. 9, 2006, now abandoned.

(60) Provisional application No. 60/651,679, filed on Feb. 9, 2005.

(51) Int. Cl.
| | |
|---|---|
| *A61B 5/145* | (2006.01) |
| *G01J 3/02* | (2006.01) |
| *G01N 21/21* | (2006.01) |
| *G01N 21/49* | (2006.01) |
| *G01N 21/47* | (2006.01) |
| *A61B 5/00* | (2006.01) |

(52) U.S. Cl.
CPC ............ *A61B 5/14558* (2013.01); *G01J 3/02* (2013.01); *G01J 3/021* (2013.01); *G01J 3/0208* (2013.01); *G01J 3/0218* (2013.01); *G01J 3/0262* (2013.01); *G01N 21/21* (2013.01); *G01N 21/49* (2013.01); *A61B 5/14546* (2013.01); *A61B 5/7257* (2013.01); *G01N 2021/4792* (2013.01)

(58) Field of Classification Search
USPC ........................................................ 356/364
See application file for complete search history.

(56) References Cited

U.S. PATENT DOCUMENTS

| | | | | |
|---|---|---|---|---|
| 5,788,632 | A * | 8/1998 | Pezzaniti | G01N 21/21 356/368 |
| 5,847,394 | A * | 12/1998 | Alfano | A61B 1/042 250/341.1 |
| 5,956,144 | A * | 9/1999 | Kaplan | G01J 4/00 356/364 |
| 6,070,093 | A * | 5/2000 | Oosta | A61B 5/0095 356/39 |
| 6,177,984 | B1 * | 1/2001 | Jacques | G01J 4/00 356/338 |
| 6,404,497 | B1 * | 6/2002 | Backman | A61B 5/0084 356/369 |
| 6,567,678 | B1 * | 5/2003 | Oosta | A61B 5/0095 356/364 |
| 6,587,711 | B1 * | 7/2003 | Alfano | A61B 5/0068 600/410 |
| 2006/0178570 | A1 * | 8/2006 | Robinson | A61B 5/14558 600/310 |
| 2011/0184260 | A1 * | 7/2011 | Robinson | A61B 5/14532 600/316 |

* cited by examiner

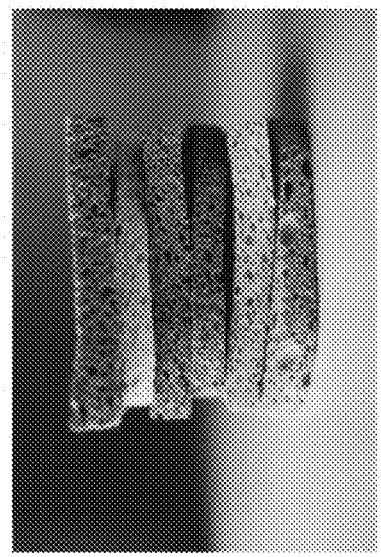
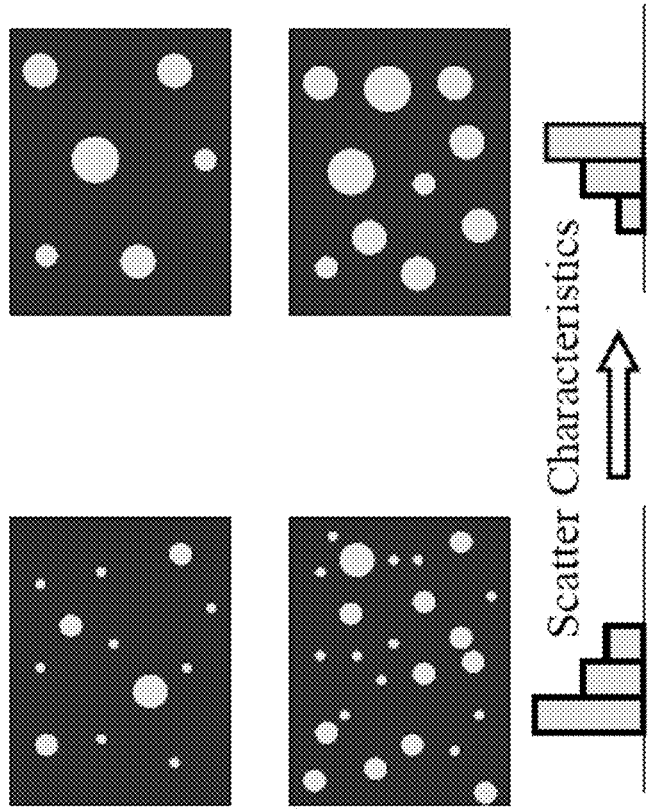
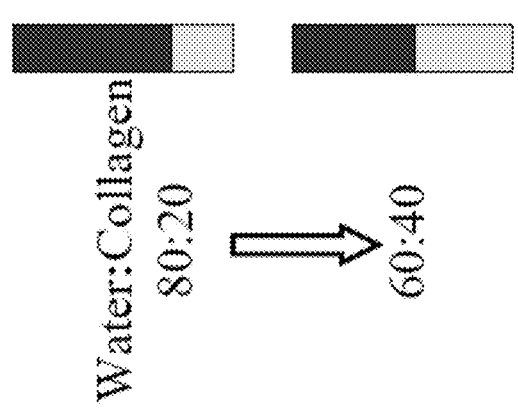
Figure 1

Figure 4 Tissue sampler using polarized light

Figure 7 Distribution of path lengths making up total signal at various polarizer angles Figure 9 Variable Path length Sampler using Translation Stage Figure 10 Multiple Path Length Sampler Using Multiple detectors Figure 11 Multiple path length sampler using multiple optical fibers and detectors

Figure 24
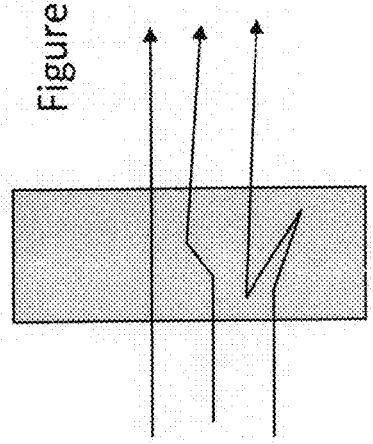
Figure 24B
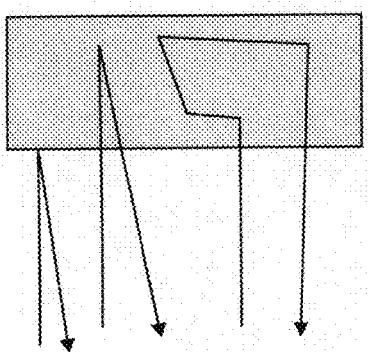
Figure 24C
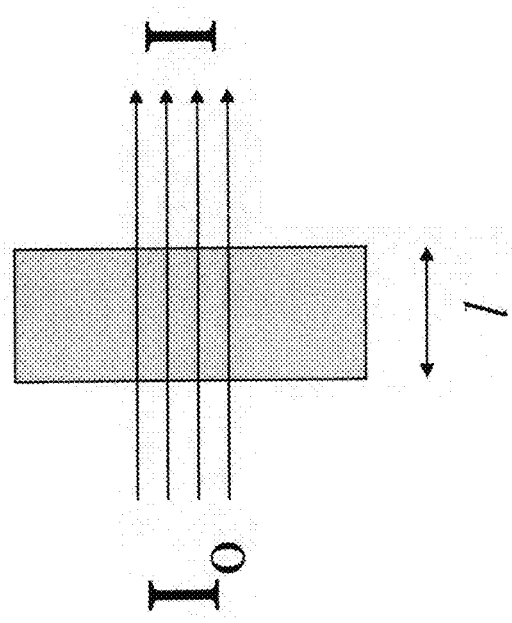
Figure 24A

METHODS AND APPARATUSES FOR NONINVASIVE DETERMINATIONS OF ANALYTES

CROSS-REFERENCE TO RELATED APPLICATIONS

This application claims priority as a continuation in part of U.S. application Ser. No. 13/036,012, filed Feb. 28, 2011, and to the applications to which application Ser. No. 13/036,012 claimed priority. U.S. application Ser. No. 13/036,012 claimed the benefit of U.S. provisional application 60/651,679, filed Feb. 9, 2005, and was a continuation in part of U.S. application Ser. No. 11/350,916, filed Feb. 9, 2006. Each of the foregoing applications is incorporated herein by reference.

BACKGROUND OF THE INVENTION

This invention relates to a system for measurement of material properties by determination of the response of a sample to incident radiation, and more specifically to the measurement of analytes such as glucose or alcohol in human tissue.

Noninvasive glucose monitoring has been a long-standing objective for many development groups. Several of these groups have sought to use near infrared spectroscopy as the measurement modality. To date, none of these groups has demonstrated a system that generates noninvasive glucose measurements adequate to satisfy both the U.S. Food and Drug Administration ("FDA") and the physician community. The potential use of near-infrared (near-IR) spectroscopy for noninvasive glucose measurements has attracted significant recent attention. Infrared spectroscopy (IR spectroscopy) is the spectroscopy that deals with the infrared region of the electromagnetic spectrum, that is light with a longer wavelength and lower frequency than visible light. It covers a range of techniques, mostly based on absorption spectroscopy. As with all spectroscopic techniques, it can be used to identify, measure, quantify and study chemicals. The infrared portion of the electromagnetic spectrum is usually divided into three regions; the near-, mid- and far-infrared, named for their relation to the visible spectrum. The higher energy near-IR, approximately 14000-4000 cm-1 (0.8-2.5 µm wavelength) can excite overtone or harmonic vibrations.

Some principles behind a near infrared spectroscopic measurement include (1) to allow near-IR light to penetrate a region of body tissue and thereby excite vibrations in the constituent molecules; (2) to measure the amount of light absorbed as a function of wavelength; and (3) to use the resulting data to construct a calibration model that relates the spectral information to the concentration of blood glucose. The generation of this calibration model requires the measurement of reference glucose concentration values during the spectral data acquisition, typically through the collection of blood samples and the use of a conventional clinical glucose analyzer. The calibration model can be used subsequently to predict unknown glucose concentrations.

The construction of a successful calibration model requires the extraction of glucose-dependent information from the spectral background produced by the body tissue. Inspections of spectra collected from concentrated glucose solutions reveal significant glucose absorption bands centered at wavelengths of 1.67, 2.13, 2.27, and 2.33 µm. These bands arise from combination and overtone molecular vibrations associated with C—H and O—H bonds of the glucose molecule. The principal near-IR absorbers in tissue are water, proteins, and fat. Each is present in significantly greater quantity than glucose, and the spectral signals arising from each of these species overlap with one or more of the glucose absorption bands. The presence of overlapping spectral signatures dictates that the optical measurement must be made over multiple wavelengths, (Gary Small, Leeos Newsletter, Volume 12, Number 2, April 1998). NIR spectra of aqueous systems show weak, broad and overlapping bands with random baselines. The position and intensity of the signals vary according to the chemical vicinity (hydrogen bonding effects). The influence of dissolved salts and temperature on the NIR spectra of aqueous systems is well known. Since the normal proportion of glucose in blood and tissue is only about 0.1% of the water content the spectral variations due to glucose concentration are extremely small. Due to overlapping interferences and the small size of the glucose signal, the number of wavelengths required for glucose measurement has been said to be at least 12. Thus, the overall signal-to-noise of the raw data comprising a set of light intensity values collected over a series of spectral resolution elements (wavelengths) can affect the ultimate accuracy of the system.

In addition, at wavelengths where the tissue is absorbing strongly, the precision of the optical measurement can be degraded because the amount of light escaping (diffusely reflected) from the tissue does not produce a large signal. Specifically, most of the optical light is absorbed or scattered by the tissue. The simple use of larger more powerful light sources is limited as tissue heating occurs resulting in tissue damage. Although data processing is capable of enhancing the signal-to-noise ratio (SNR) of near infrared spectroscopic data and sophisticated multivariate data processing algorithms (i.e., partial least squares (PLS) regression and/or artificial neural networks (ANN)) are desired to selectively extract the glucose-dependent spectral information, the quality of the raw spectral information drives the ultimate analytical performance and the successful implementation of noninvasive measurements. (Jason J. Burmeister and Mark A. Arnold, "*Spectroscopic Considerations for Noninvasive Blood Glucose Measurements with Near Infrared Spectroscopy*" Leeos Newsletter, Volume 12, Number 2, April 1998).

Spectroscopic noise introduced by the tissue media is an additional reason for the failure to create a clinically accurate noninvasive system. Tissue noise can include any source of spectroscopic variation that interferes with or hampers accuracy of the analyte measurement. Changes in the optical properties of tissue can contribute to tissue noise. The measurement system itself can also introduce tissue noise, for example changes in the system can make the properties of the tissue appear different. Tissue noise has been well recognized in the published literature, and is variously described as physiological variation, changes in scattering, changes in refractive index, changes in pathlength, changes in water displacement, temperature changes, collagen changes, and changes in the layer nature of tissue. See, e.g., Khalil, Omar: Noninvasive glucose measurement technologies: an update from 1999 to the dawn of the new millennium. Diabetes Technology & Therapeutics, Volume 6, number 5, 2004. Variations in the optical properties of tissue can limit the applicability of conventional spectroscopy to noninvasive measurement. Conventional absorption spectroscopy relies on the Beer-Lambert-Bouger relation between absorption, concentration, pathlength, and molar absorptivity. For the single wavelength, single component case:

$$I_\lambda = I_{\lambda,o} 10^{-\epsilon_\lambda lc}$$

$$a_\lambda = \epsilon_\lambda lc$$

Where $I_{\lambda,o}$ and $I_\lambda$ are the incident and excident flux, $e_l$ is the molar absorptivity, c is the concentration of the species, and l is the pathlength through the medium. $a_l$ is the absorption at wavelength 1 ($-\log_{10}(I_\lambda/I_{\lambda,o})$). These equations assume that photons either pass through the medium with pathlength l, or are absorbed by the molecular occupants.

In tissue, the attenuation of light is described according to light transport theory by the effective attenuation coefficient $\mu_{eff}$, i.e.:

$$I = I_0 e^{-\mu_{eff} l}$$

Where:

$$\mu_{eff} = \sqrt{3\mu_a(\mu_a + \mu'_s)}$$

Light propagation in tissue is governed by a set of spectroscopic properties; the absorption coefficient $\mu_a$, the scattering coefficient $\mu_s$, the refractive index of the cells and the interstitial fluid; and the anisotropy factor g (the average cosine of the angle at which a photon is scattered). Another set of properties are the transport properties, such as the reduced scattering coefficient $\mu'_s$, where $\mu'_s = \mu_s[1-g]$. The absorption coefficient $\mu_a$ equals the absorbance per unit path length, 2.303 EC cm-1, where E is the molar absorptivity and C is the molar concentration. As one can ascertain from the above equation, changes in tissue scattering and/or tissue absorbance will change the effective path length. As Beer's law assumes a constant pathlength such changes are quite problematic from the perspective of accurate blood glucose measurements.

Unfortunately, optical measurement of tissue does not match the assumptions required by Beer's law. Variations in tissue between individuals, variations in tissue between different locations or different times with the same individual, surface contaminants, interaction of the measurement system with the tissue, and many other real-world effects can prevent accurate optical measurements.

The process of realizing an operational and clinically useful noninvasive glucose monitoring device can require that the system obtains high quality and high signal-to-noise spectra with multiple wavelengths utilizing and optical sampling methodology that effectively samples the tissue without introducing additional variances.

SUMMARY OF THE INVENTION

The present invention provides methods and apparatuses for accurate noninvasive determination of tissue properties and analytes such as glucose by satisfying a unique set of requirements to include: (1) measurement of multiple wavelengths (greater than 12) with high signal-to-noise while concurrently not burning the tissue, (2) procuring high quality spectroscopic data in a reasonable period of time and (3) optically sampling the tissue in a repeatable manner where mechanical alteration of the tissue is reduced (as compared with previous methods) during sampling and the measured photons are preferentially selected so as to contain analyte or glucose information. Embodiments of the present invention utilize optical systems that utilize a multiplex advantage, often referred to as a Fellgett's advantage. Systems with a multiplex advantage will have improved signal-2-noise relative to a dispersive spectrometers due to the fact that multiple wavelengths are collected simultaneously but can be subsequently resolved, This results in greater optical efficiency resulting in better signal-to-noise. In the simplest of terms, a multiplexing spectrometer enables the simultaneous recording of multiple wavelengths resulting in improved signal-to-noise. The present invention can utilize systems that have a throughput or Jacquinot's advantage over existing scanning (dispersive) spectrometers. A Jacquinot's advantage results from the fact that, in a dispersive instrument, the monochromator has entrance and exit slits which restrict the amount of light that passes through it. The interferometer throughput is determined only by the diameter of the collimated beam corning from the source.

Some embodiments of the present invention utilize interferometers. Interferometry refers to a family of techniques in which electromagnetic waves are superimposed in order to extract information about the waves. Interferometry makes use of the principle of superposition to combine separate waves together in a way that will cause the result of their combination to have some meaningful property that is diagnostic of the original state of the waves. This works because when two waves with the same frequency combine, the resulting pattern is determined by the phase difference between the two waves—waves that are in phase will undergo constructive interference while waves that are out of phase will undergo destructive interference. Fourier transform infrared spectroscopy (FTIR) is a interferometry technique which is used to obtain an infrared spectrum of absorption. An FTIR spectrometer simultaneously collects spectral data in a wide spectral range. This confers a significant advantage over a dispersive spectrometer which measures intensity over a narrow range of wavelengths at a time. The term Fourier transform infrared spectroscopy originates from the fact that a Fourier transform (a mathematical algorithm) can be used to convert the raw data into the actual spectrum. An objective of any absorption spectroscopy is to measure how well a sample absorbs light at each wavelength. The most straightforward way to do this, the "dispersive spectroscopy" technique, is to shine a monochromatic light beam at a sample, measure how much of the light is absorbed, and repeat for each different wavelength.

Fourier transform spectroscopy is a less intuitive way to obtain the same information. Rather than shining a monochromatic beam of light at the sample, this technique shines a beam containing many different frequencies of light at once, and measures how much of that beam is absorbed by the sample. Next, the beam is modified to contain a different combination of frequencies, giving a second data point. This process is repeated many times. Afterwards, a computer takes all these data and works backwards to infer what the absorption is at each wavelength.

Three principle advantages for a FT spectrometer compared to a scanning (dispersive) spectrometer are (1) the multiplex also known as Fellgett's advantage, this arises from the fact that information from all wavelengths is collected simultaneously. It results in a higher signal-to-noise ratio for a given scan-time or a shorter scan-time for a given resolution. (2) Jacquinot's advantage, this throughput advantage results from the fact that, in a dispersive instrument, the monochromator has entrance and exit slits which restrict the amount of light that passes through it. The interferometer throughput is determined only by the diameter of the collimated beam coming from the source. It also results in a higher Signal-to-noise ratio for a given scan-time or a shorter scan-time for a given resolution. (3) Stray light rejection or reduced sensitivity, monochromators are sensitive to stray light interferences and must be enclosed to eliminate external polychromatic radiation. An FTIR detector responds to intensity modulations produced by the interferometer. Although stray light does contribute to detector saturation in a FTIR, it is not modulated and therefore does not contribute to the spectral intensities measured.

Although less common than the FTIR, multiplexing spectrometers also have advantages over monochomators. A Hadamard Transform Spectrometer is a multiplexing spectrometer based on a 127 square cyclic Hadamard matrix. The system creates a multiplexing gain factor of over five-fold in signal-to-noise ratio over use of a conventional single exit slit monochromater at similar resolution. Other types of multiplexing schemes can be used as well as other methods to encode wavelength information so a multiplex advantage can be obtained.

Acousto-optic tunable filters (AOTF) are solid-state electronically tunable spectral bandpass filters which operate on the principle of acousto-optic interaction in an anisotropic medium. The AOTF utilizes an anisotropic, birefringent AO medium for its operation. An AOTF is well suited to high-frequency optical switching and wavelength selection. With injection of a combination of radio-frequency signals into its transducer, the AOTF acts as an electronically controllable, multiplexing spectrometer. J. F Turner and P. J. Treado demonstrated "Near-Infrared Acousto-Optic Tunable Filter Hadamard Transform Spectroscopy" Applied Spectroscopy, Vol. 50, Issue 2, pp. 277-284 (1996) demonstrated a multiplexing AOTF based upon a Hadamard transform. In operation, the integrated intensity on the detector measures combinations of the diffracted wavelengths. The light encodement is performed without the use of physical masks and is governed by HT mathematics, which allow efficient recovery of the optical spectrum. Appreciable signal-to-noise enhancement is demonstrated with the HT AOTF spectrometer. Other types of multiplexing spectrometers exist but as stated above the most common is the FTIR.

The ability to make accurate noninvasive optical measurements benefits from the ability to procure stable and repeatable tissue spectra. Contact based forearm sampling systems have been subject to tissue compression during the measurement and can alter the fluid status of the tissue volume under examination. Additionally, site-to-site variation due to an inability to sample the same area of tissue adds additional measurement variance. These spectral variances can create undesirable spectral noise and effectively decrease the system's signal-to-noise ratio. The present invention can address these issues through an improved optical sampling method that addresses these sources of spectral noise. Embodiments of the present invention provide a non-contact optical sampling system based upon diffuse reflectance measurements from the tissue, typically the back of the finger is disclosed. The system uses cross polarization, which can preferentially eliminate those photons associated with epidermal reflection and to preferentially collect those photons that have undergone multiple scattering events so that the photons polarization had become randomized. The illumination light is passed through a polarizer and defines an illumination orientation. The collected light can then be passed through a second polarizer. The orientation difference between the illumination polarizer and the collection polarizer determines what type of light is preferentially selected. A parallel or zero degree difference between the illumination and analyzer polarizers emphasizes light that has maintained the same polarization state. Light from reflected from the skin surface is most likely to maintain its original polarization state. In practice the parallel polarization orientation will accept photons reflected from the air/skin surface (also referred to as specular light or short path light) and rejecting half of the diffusely reflected light (subsurface scattering). The specular or surface reflection photons contain little glucose information and can add noise to the spectral measurement. A perpendicular or 90 degree relationship between the illumination and collection polarizers will suppress the skin surface reflections and emphasizes the subsurface skin structures by rejecting the surface glare and accepting half of the diffusely reflected light. The diffusely reflected light consists of photons that have penetrated deeply into the skin and have been depolarized by the birefringent dermal collagen fibers. Due to the increased depth of penetration, these photons have interacted with body fluids containing metabolic analytes such as glucose. Therefore, the use of polarization as a photon selection methodology for those photons that contain glucose information is a useful element of the measurement system.

The concept of using cross polarization for the rejection of superficial glare has been used in a variety of imaging systems. R. R. Anderson, "Polarized light examination and photography of the skin," *Arch. Dermatol.* 127, 1000-1005 (1991) reported on the dermatologic practice of illuminating with linearly polarized light and observing through a linear polarizer oriented perpendicular to the orientation of the illumination light so as to avoid surface glare. R. R. Anderson, "Polarized light examination and photography of the skin,"*Arch. Dermatol.* 127, 1000-1005 (1991). J. M. Schmitt, A. H. Gandjbakhche, and R. F. Bonner, "Use of polarized light to discriminate short-path photons in a multiply scattering medium," *Appl. Opt.* 32, 6535-6546 (1992), reported on the loss of the degrees of linear and circular polarization as linearly and circularly polarized light propagates in light scattering media. S. L. Jacques, M. R. Ostermeyer, L. Wang, and D. Stephens, "Polarized light transmission through skin using video reflectometry: Toward optical tomography of superficial tissue layers," *Proc. SPIE* 2671, 199-210 (1996), reported on the point-spread function of reflected polarized light in turbid media and proposed the use of polarized light for reflectance video imaging of superficial tissues. M. R. Ostermeyer, D. V. Stephens, L. Wang, and S. L. Jacques, "Nearfield polarization effects on light propagation in random media," in: *OSA TOPS on Biomedical Optical Spectroscopy and Diagnostics*, E. Sevick-Muraca and E. Benaron, Eds., Vol. 3, pp. 20-25, Optical Society of America, Washington, D.C. (1996), considered a two-scatter model that explained the cross-shaped point-spread function of reflected linearly polarized light in microsphere solutions when observed through a linear polarizing filter. They demonstrated that the point-spread function in skin was minimal which suggested that reflected polarized light imaging in skin would not suffer significant blurring and therefore imaging of superficial skin was feasible. S. G. Demos and R. R. Alfano, "Optical polarization imaging," *Appl. Opt.* 36, 150-155 (1997), demonstrate a technique that allows for optical imaging of a surface as well as structures beneath the surface of a scattering medium in the retroreflection geometry. The technique is based on polarization gating. The sample recorded with the polarization axis of the analyzer parallel (parallel image) and perpendicular (perpendicular image) to the polarization of the illuminating light. It is shown that the surface image information is almost completely carried by the parallel image whereas the perpendicular image contains information predominantly from beneath the surface. By the use of the perpendicular polarization component and different illuminating wavelengths, it is demonstrated that images of structures at different depths can be obtained.

A. H. Hielscher, J. R. Mourant, and I. J. Bigio, "Influence of particle size and concentration on the diffuse backscattering of polarized light from tissue phantoms and biological cell suspensions," Appl. Opt. 36, 125-135 (1997) pursued CCD camera imaging of reflected polarized light in microsphere solutions and reported on how particle size influences the cross-shaped pattern. They also showed that cell solutions could replace microsphere solutions and provide a cross-shaped pattern for analysis.

More recently S. L. Jacques, J. C. Ramella-Roman and K. Lee, "Imaging skin pathology with polarized light", Journal of Biomedical Optics 7(3), 329-340 (July 2002) demonstrated a modification of the cross polarization imaging technique by acquiring two images through and analyzing linear polarizer in front of the camera. One image ($I_{par}$) is acquired with the analyzer oriented parallel to the polarization of illumination and second image ($I_{per}$) acquired with the analyzer oriented perpendicular to the illumination. An image based on the polarization ratio is created. The resulting images are able to emphasize image contrast on the basis of light scattering in the superficial layers of tissue.

In addition to these publications, the concept of using cross polarization for tissue imaging can be found in U.S. Pat. No. 5,847,394 by Alfano et al "Imaging of objects based upon the polarization board deep polarization of light and U.S. Pat. No. 6,587,711 by Alfano et al. "Spectral polarizing tomographic dermatoscope". U.S. Pat. No. 5,847,394 discloses an optical sampler comprising an illumination system configured to communicate light having a first polarization to the tissue in an imaging mode. The optical sampler contains a second collection polarizer for collecting the light after interaction with the tissue and directing said image to a CCD array. FIG. 7 is an overall schematic associated with the optical imaging system. U.S. Pat. No. 6,587,711 describes a measurement system composed of non-imaging components (fiber optics) coupled with a monochromatic illumination scheme (Col. 5, lines 23 to Col. 6, line 17). Specifically, the system is composed of a first, second and third illuminating means that can be actuated in a variety of manners. The data acquisition methodology defined results in the illumination of the tissue and subsequent data acquisition by each LED individually. Specifically, "Red, green, blue, and white LED's are disposed within the handle portion of the housing and are electrically connected to a battery also disposed within the handle portion of the housing. A manually-operable switch for controlling actuation of each of the four LED's is accessible on the handle portion of the housing" abstract of U.S. Pat. No. 6,587,711. The patent also states that "apparatus 11 also includes said first, second and third illuminating means to permit the selective activation by an operator of said first, second and third illuminating means either individually or in various combinations. The result is a LED spectrometer where the change in light source (LED) enables the sampling of the tissue under different illuminations or illumination wavelegths. This method of sampling creates a one-to-one relationship between the input information (illumination light) and the measured output (measured intensity). The result is four light intensity values collected over different illumination wavelengths.

The system described by Alfano does not provide the information content necessary for noninvasive glucose measurements nor is the limited information obtained at a high enough signal to noise ratio to enable measurement. The system does have the capability of utilizing a multiplex or Fellgett's advantage for improved signal-to-noise. Additionally the system does not have the capability of utilizing Jacquinot's advantage for improved signal-to-noise. As a final note, the LEDs are not modulated so that the system will be very sensitive to stray light contamination. As noted above and cited in the literature, the noninvasive measurement of glucose requires sufficiently high signal-to-noise to permit a reliable differentiation between glucose dependent signals and signals generated by other matrix components. Additionally, due to the overlapping interferences present, multiple wavelengths (12 or more) must be utilized to effectively extract the glucose signal from other interferences. Therefore, such a system utilizing an LED spectrometer with cross polarization sampling will not enable the noninvasive measurement of glucose at clinically relevant levels.

The system disclosed herein addresses these issues by utilizing a Fourier transform infrared spectrophotometer coupled with a noncontact cross polarization tissue measurement system. The use of a Fourier transform infrared spectrophotometer enables the procurement of high signal-to-noise spectral data through the use of both the Fellgett's advantage and Jacquinot's advantage. The use of a FTIR creates a many-to-many relationship. The input information is multi-wavelength in its content and the output is multiple wavelength intensities. Additionally, the system utilizes a noncontact sampling methodology so that physical perturbation of the tissue does not occur. Stray light contamination a significant issue with non-contact sampling is limited due to the use of a modulated signal by the FTIR instrumentation.

The use of an optical smoothing agent on the finger further improves the signal-to-noise of the resulting spectra. Reduction of site-to-site repositioning errors is possible due to the many fiducial features on the finger. These features can be used to ensure proper realignment prior to the initiation of sampling. Some embodiments of the present invention comprise an optical sampler having an illumination subsystem, adapted to communicate light having a first polarization to a tissue surface; a collection subsystem, adapted to collect light having a second polarization communicated from the tissue after interaction with the tissue; wherein the first polarization is different from the second polarization. The difference in the polarizations can discourage collection of light specularly reflected from the tissue surface, and can encourage preferential collection of light that has interacted with a desired depth of penetration or path length distribution in the tissue. The different polarizations can, as examples, be linear polarizations with an angle between, or elliptical polarizations of different handedness.

A smoothing agent can be applied to the tissue surface to discourage polarization changes in specularly reflected light, enhancing the rejection of specularly reflected light by the polarization difference. The spectroscopic features of the smoothing agent can be determined in resulting spectroscopic information, and the presence, thickness, and proper application of the smoothing agent verified. The illumination system, collection system, or both, can exploit a plurality of polarization states, allowing multiple depths or path length distributions to be sampled, and allowing selection of specific depths or path length distributions for sampling. The rejection of specularly reflected light by polarization allows the sampler to be spaced from the tissue, reducing the problems attendant to contact samplers (e.g., tissue measurement trends due to pressure or heating). Separation of the sampler from the tissue enables a large area, e.g., 20 mm$^2$, to be sampled. The illumination system and collection system can be disposed so as to communicate with different portions of the tissue surface, e.g., with portions that are separated by a fixed or variable distance.

The illumination system and collection system can be configured to optimize the sampling of the tissue, for example by changing the optical focus or the distance from the tissue surface in response to interface quality detector (e.g., an autofocus system, or a spectroscopic quality feedback system). The portion of the tissue sampled can be identified with a tissue location system such as an imaging system that images a component of the vascular system, allowing measurements to be made at repeatable locations without mechanical constraints on the tissue.

Advantages and novel features will become apparent to those skilled in the art upon examination of the following description or may be learned by practice of the invention. The advantages of the invention may be realized and attained by means of the instrumentalities and combinations particularly pointed out in the appended claims.

BRIEF DESCRIPTION OF THE DRAWINGS

FIG. 1 is a schematic illustration of tissue and its variances.

FIG. 24 is a plot of degree of polarization measurements made on scattering solutions samples with varying amounts of scatter.

DETAILED DESCRIPTION OF THE INVENTION

Figure 2:
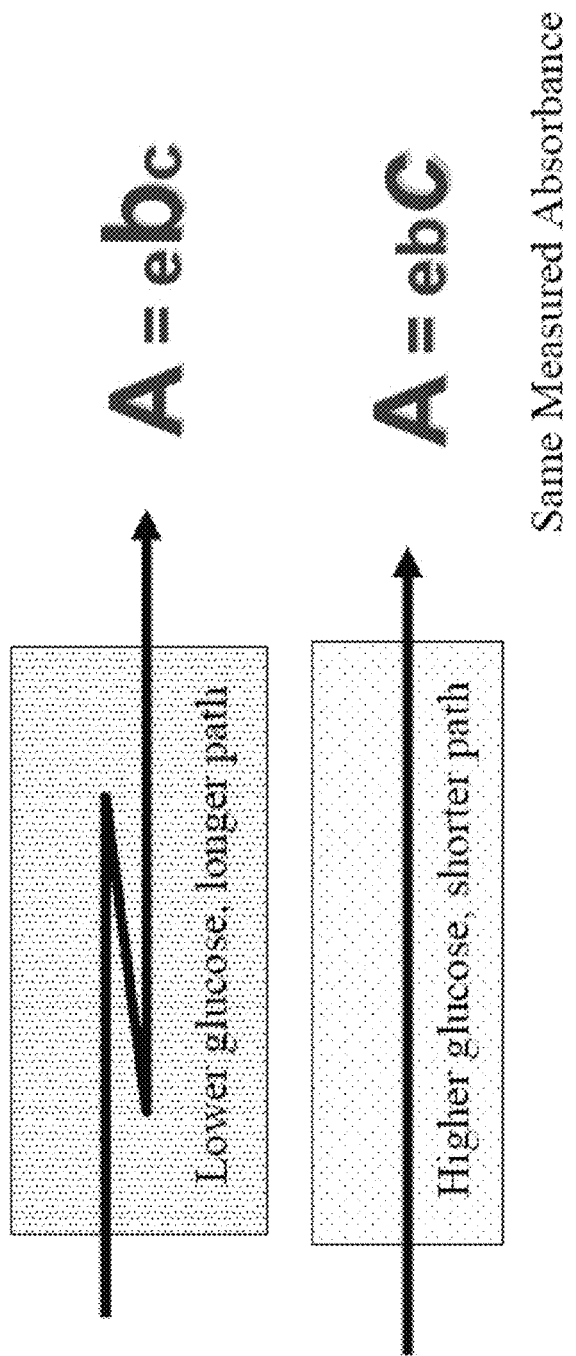
FIG. 2 is a schematic illustration of the limitations of Beer's law in scattering media.

The pathlength assumptions used for Beer's law are not well satisfied in the realities of making measurements in human tissue. In a medium such as tissue, photons are scattered and do not travel a single path but instead travel a distribution of paths. The distribution of paths results in a distribution of pathlengths (the length of a path traveled by a photon; a set of pathlengths having a particular distribution of lengths a "pathlength distribution" or "PLD"). In simple terms, this distribution will have a number of rays that traveled the typical path length, as well as rays that traveled shorter and longer paths through the sample via the random nature of scattering interactions. The properties of this path length distribution can be further characterized with statistical properties, such as the distribution's mean and standard deviation. These properties are not necessarily fixed for a measurement system as they can depend, in complex ways, on sample properties including the number of scattering particles, size and shape of the scatter particles, and wavelength. Additionally, the PLD of a specific volume of tissue is sensitive to the inherent properties of the tissue as well as the way in which the tissue is sampled. Any change in the PLD between noninvasive measurements or during a noninvasive measurement will cause a change in path such that the assumptions of Beer's law are not satisfied. The net result is an error in the noninvasive measurement. Changes in the optical properties cause changes in the observed PLD. Changes in the PLD can result in analyte measurement errors.

Simplified Physical Model.

A simplified model can be useful in understanding the principles of operation of the present invention. With recognition that tissue is a very complex layered media, a simplifying physical model provides a useful construct for explanation and dissection of the problem into simpler parts. Consider the case of making a spectroscopic measurement in a layered set of sponges. The sponges resemble tissue in that sponges have a solid structure with surrounding fluid. This physical model is similar to tissue in that tissue has a solid matrix composed of cells and collagen surrounded by interstitial fluid. This physical model of a sponge and its relationship to tissue will be systematically described with increasing complexity.

Consider a sponge as a heterogeneous structure. Depending on the size of the sampling area relative to the variation in the sponge, different observations of the sponge at different locations can look quite different. Tissue is a heterogeneous medium and thus location to location differences can exist.

Consider the simplified case where two sponges have the same composition but different densities. Density defined here as the ratio of solid sponge material to either air (if dry) or water (if wet) per unit volume. These density differences will cause changes in the light propagation characteristics due to changes in scatter. These differences will then translate into differences in the PLD between sponges. The collagen to water relationship differs in tissue and causes differences in the observed PLD.

Water is able to move into and out of the sponge based upon compression. Compression changes the density of the sponge in a transient manner and thus changes the observed PLD. Tissue is a compressible medium as evidenced by the indents one can make in tissue. Thus, compression of tissue can change the water to collagen ratio and alters the observed PLD.

Skin is composed of different skin layers, similar to a stack of sponges. Each layer in a layered stack of sponges can be of different thickness, and can have different properties (e.g., different densities). The differences in the thickness and other properties of the sponge layers can modify the optical properties of the stack and can cause a change in the observed PLD. The skin thickness of people can vary, e.g., between men and women, and as a result of aging. Thus, differences in skin thickness can cause changes in the optical properties of the media and the observed PLD. See FIG. 1 for a graphical representation of the above concepts.

Returning to Beer's law:

$$a_\lambda = \epsilon_\lambda l c$$

where $I_{\lambda,o}$ and $I_\lambda$ are the incident and excident flux, $e_l$ is the molar absorptivity, c is the concentration of the species, and l is the pathlength through the medium, $a_l$ is the absorption at wavelength l. The same recorded absorbance can be obtained if the product of pathlength and concentration are maintained, see FIG. 2. Stated differently, the absorbance information can not distinguish between changes in path and changes in concentration. Returning to the sponge analogy, consider a hydrated sponge with the water in the sponge at a fixed glucose concentration. If the sponge is compressed, the glucose concentration of the fluid remains the same, yet the amount of scatter or solid matter per unit volume increases. This increase in scatter can increase the optical pathlength, and consequently the optically measured glucose concentration can be higher despite the fact that the actual glucose concentration of the fluid has remained unchanged. Further complicating the application of Beer's law to even this simple system is the fact that the amount of fluid per unit volume decreases during compression, such that the relative contributions of fluid, glucose, and solid matter change resulting in PLD variations. With an objective of improved analyte measurements, decreased amount of path length change or effectively compensating for path length changes can lead to improved analyte measurements. Noninvasive glucose measurements in tissue have concentration and path variations that results from changes in absorber and scatter levels. The simple schematic in FIG. 2 does not show that pathlength also varies with the physical dimensions of the sample and that total absorbance varies with multiple concentrations.

Sources and Causes of Tissue Noise.

The following discussion of sources of tissue noise and their resulting influence on pathlength distribution can help understand the operation and benefits of various aspects of the present invention.

Inherent Differences Between People.

Human tissue is a complex structure composed of multiple layers of varying composition and varying thickness. Structural differences between people influence how light interacts with the tissue. Specifically, these tissue differences can cause changes in the scattering and absorption characteristics of the tissue. These changes in turn cause changes in the PLD. In experiments with more than a hundred different people, the PLD has been found to differ significantly between people.

Tissue Heterogeneity Differences.

Human tissue is a complex structure composed of multiple layers of composition and varying thickness. Additionally, tissue can be highly heterogeneous with site-to-site differences. For example, skin on a person's palm is quite difference from skin on the same person's forearm or face. These structural differences between varying locations can influence how light interacts with the tissue. Experimental data indicates that the PLD differs depending upon the exact location sampled. Sampling the same tissue volume, or at least tissue volumes that largely overlap, with each repeat sampling of the tissue can reduce the PLD differences. For a given amount of overlap, a very small sampling area will have very tight requirements on repositioning error while a larger sampler will have less stringent requirements. In human testing with a fiber optic sampler we have observed that repositioning errors of only a few millimeters can create significant spectral differences. These spectral differences due to site-to-site differences cause changes in the PLD and result in prediction errors. Thus, a sampling system that samples a large area with a significant amount of overlap between adjacent samples has distinct advantages.

Tissue samplers (sometimes known as optical probes) that obtain optical data at multiple path lengths are susceptible to PLD differences. In multi-path samplers that use a different physical separation between the illumination and collection sites to generate different paths, slightly different locations of the tissue are sampled, introducing additional tissue noise.

Tissue Compression Issues.

In addition to the inherent PLD differences described above, tissue is not a static structure and the PLD can change appreciably during the measurement period. As an example, consider the imprint left in tissue when skin is placed in pressure contact with any hard object. When sampling the arm with a solid lens or surface, the tissue can become slightly compressed during the sampling period. The compression of the tissue occurs due to movement of water and the compression of the underlying collagen matrix. The water and collagen changes result in both absorption (composition) changes and changes in scatter. The influence of contact sampling on absorption and scattering coefficients is described in U.S. Pat. No. 6,534,012. The patent describes a moderately complex system for controlling the pressure exerted on the arm. Changes in the absorbance or scattering coefficients due to the sampling process results in a variable PLD during the sampling period, and a corresponding detrimental effect on measurement accuracy.

Skin Surface Issues.

In addition to internal changes, the interface between the tissue and the optical interface can also change over time. Skin is a rough surface with many wrinkles and cracks. Changes in the skin surface can occur between days, during a single day, and even during a single measurement period. Between day changes can occur, for example, due to sun exposure. Within day changes can occur, for example, due to activities such as taking a shower. Measurement period changes can occur, for example, due to changes in the air spaces or tissue cracks. As cracks or spaces decrease in size, the amount of contact between the lens and the skin improves. This improved contact can change the efficiency of light transfer into and out of the tissue and also can change the effective numerical aperture of the light entering the tissue. The numerical aperture is defined as the cone angle of the light entering and exiting the tissue. A change in the numerical aperture can cause a change in the PLD, resulting in analyte measurement errors. Sampling the tissue with a contact-based sampler can also cause the skin to perspire over the sampling period. Perspiration can change the optical coupling into the tissue and influence the measurement result.

Tissue Location Relative to Sampling System Issues.

Many tissue sampling systems are based upon an assumption that the tissue is in contact with an optically clear element or that the tissue is in a spatially repeatable location. The use of an optically clear element in contact with the skin was discussed above. The fact that tissue is not a rigid structure causes significant difficulty in satisfying the criteria associated with a spatially repeatable location. Most optical systems have a focal point (e.g. like a camera) and location of the tissue in a different position effectively blurs or degrades the spectral data. The location of the tissue, specifically the front surface plane of the tissue, is influenced by differences in the elasticity of tissue, skin tension, activation of muscles, and the influence of gravity. Differences in location can be a source of tissue noise that degrades measurement performance.

Tissue Surface Contamination Issues.

To make a useful noninvasive analyte (e.g., glucose or alcohol) measurement, radiation must interact with a material (e.g., a bodily fluid) that appropriately represents the blood or systemic value of the analyte of interest. Radiation that simply reflects off the front surface of the tissue generally contains little or no useful information, since it has little interaction with the bodily fluid. Radiation that reflects from the front surface or from very shallow depths of penetration will be referred to as specular light. Even radiation that penetrates deeply into the tissue and contains analyte information can be influenced by contaminating substances on the surface because the light passes through the layer of contamination twice. For example syrup on the arm of a patient undergoing glucose testing can result in a measurement error.

Accuracy of spectroscopic measurements in tissue can be improved by reducing the sources of tissue noise, and/or by increasing the information content of the spectral data. Generally, any sampler system that enables the procurement of spectra with a constant or more constant PLD will positively influence measurement accuracy. Any sampler system that provides more unique spectroscopic measurement scenarios (e.g., binocular vs. monocular, or controllable path length sampling) can increase the information content of the spectral data.

The present invention comprises tissue sampling systems that reduce tissue noise, and that can increase the information content of the spectral data acquired. Various embodiments of the present invention include various combinations of the following characteristics:

No contact between the sampler and the tissue. The lack of contact can reduce the influence of tissue compression as well as physiological changes at the tissue surface.

Illumination and collection optics that cover a relatively large area of tissue allowing the signal to be averaged over a large area, and thereby reducing site-to-site variations.

A means of varying the distribution of path lengths or depth of penetration through the tissue in order to exploit these differences in the data processing to arrive at a more accurate estimation of the analyte concentrations.

Ability to sample the same tissue location or have a significant amount of overlap between different samplings of the tissue. A high amount of overlap between sampling can reduce the spectral variation due to site-to-site differences.

System that compensates for differences in the location of the tissue surface and/or provides feedback to the user such that the tissue sampling site is located in a repeatable manner.

Rejection of specular light from the measured spectrum. Since specular or short path length spectral data contain little or no useful analyte information, the rejection of specular light removes or decreases another source of noise.

Example Embodiment

Figure 3:
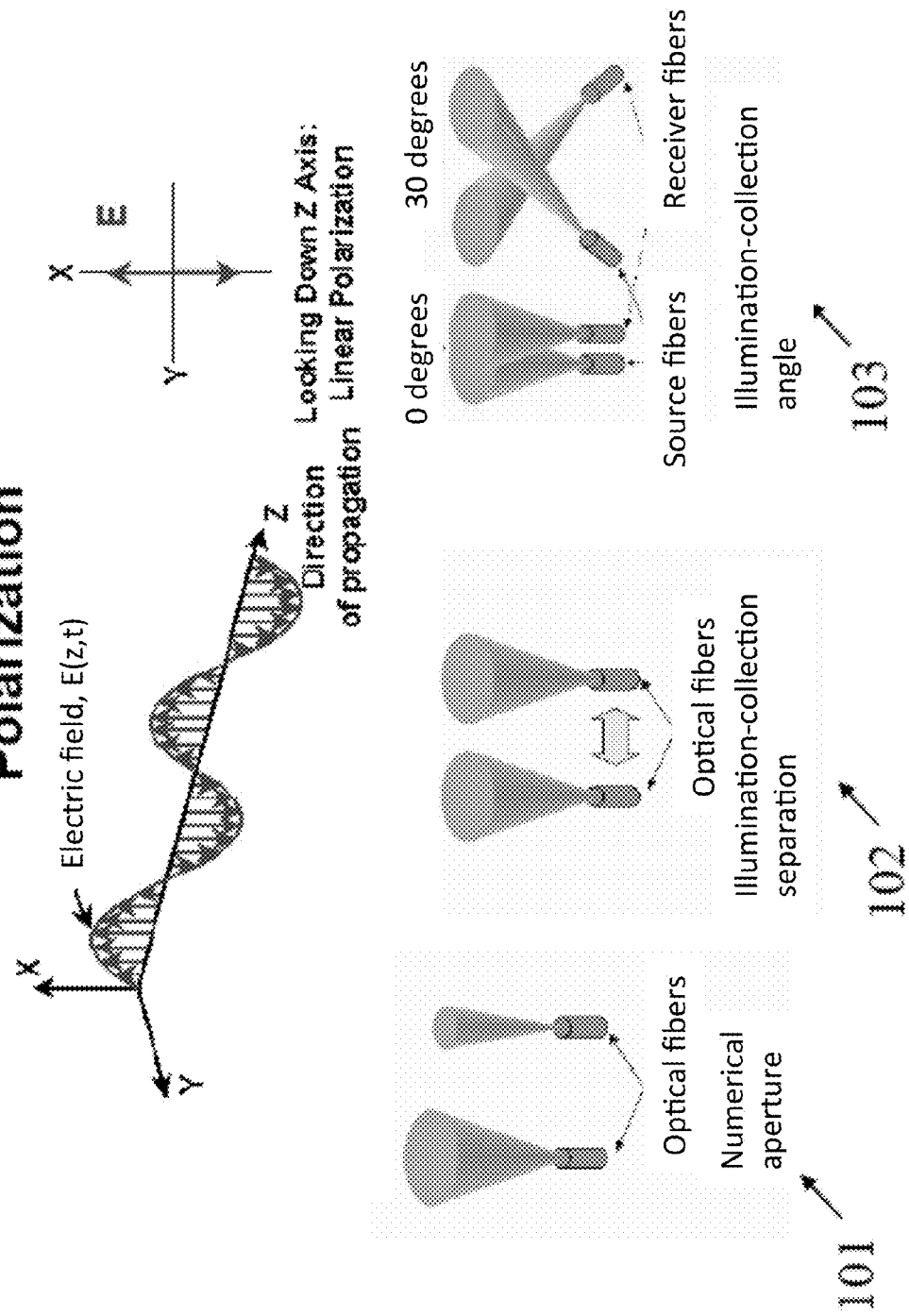
FIG. 3 is an illustration of the light properties available for control by optical samplers.

As illustrated in FIG. 3, optical samplers designed for tissue sampling have focused on controlling the numerical aperture of the light 101, the illumination and collection angles 103 and the distance between source and collection fibers 102. Relative polarization of the illumination and collection light can also be used 104.

Figure 4:
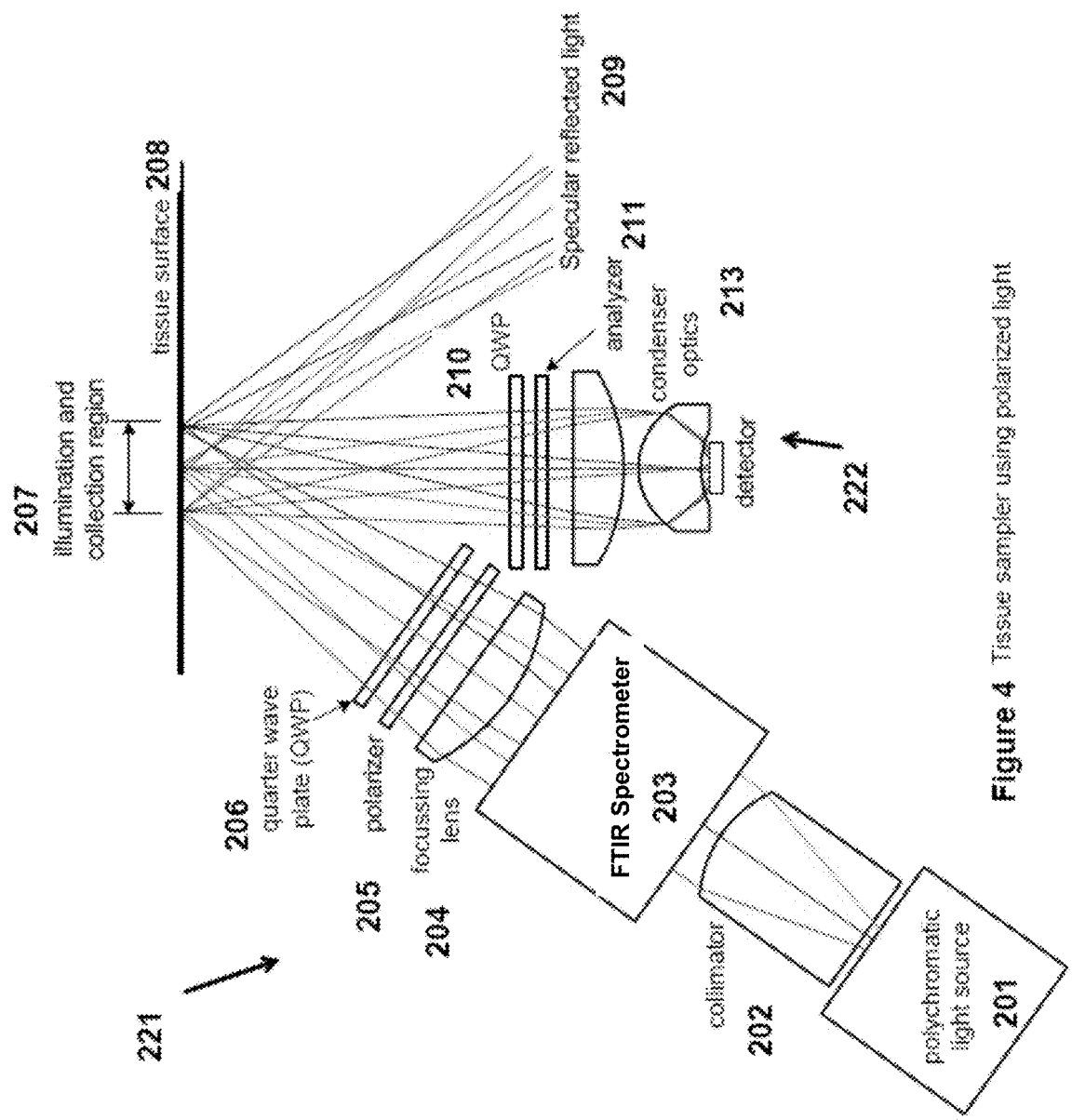
FIG. 4 is a schematic illustration of a system for noninvasive glucose monitoring according to the present invention.

FIG. 4 is a schematic illustration of a tissue sampler according to the present invention. A light source 201, e.g., a broadband light source, communicates light, e.g., by focusing or collimating element 202, to the input aperture of a multiplexing spectrometer 203, e.g. a Fourier Transform spectrometer. The spectrometer 203 communicates multiple wavelengths of light from its output port, e.g., using a focusing element 204, to a tissue surface 208. The optical path from the spectrometer 203 to the tissue surface 208 can also include a polarizer 205, a quarter wave plate 206, or both, to cause light incident on the tissue surface 208 to have controlled linear or circular polarization.

Light diffusely reflected from the tissue after interaction with the tissue can be collected by condenser optics 213 and communicated to a detector 212. The optical path from the tissue surface 208 to the detector 213 can also include a second polarizer 211 (sometimes referred to herein as an "analyzer"), a second quarter wave plate 210, or both. The illumination optics 221 and collection optics 222 can be disposed relative to each other and to the tissue surface 208 to discourage collection of specularly reflected light 209. As an example, the tissue can be placed at the intersection of the optical axis of the illumination optics 221 and the collection optics 222, with the tissue surface forming different angles with the two axes. In one implementation of the present invention, the optics were selected to illuminate an area of tissue approximately 10 mm in diameter, and a positioning apparatus (not shown) used to maintain the tissue surface at the desired location and orientation. Note that the spectrometer can be in either the illumination or the collection side.

The sampling system of FIG. 4 allows the use of the polarizer, analyzer, and quarter wave plates to vary the path length distribution of the light collected from scattering in the tissue. Data collected from two or more path length distributions can be used to detect differences in quantities such as the scattering coefficient of the tissue; a calibration model can take advantage of this information to improve analyte measurement accuracy (e.g., by deconvolving the covariance of fluid concentration and PLD). As discussed earlier, human tissue is a very complex material. Tissue particles vary in shape and size, with sizes varying between about 0.1 and 20 microns. For a spectrometer operating in the 1.0 to 2.5 micron wavelength range the particle sizes vary from roughly $\frac{1}{10}$ the shortest wavelength to nearly 10 times the longest wavelength. The particle scattering and polarization phase functions can vary markedly over this particle size range. Material such as collagen also forms oriented strands, presenting the tissue as an anisotropic medium for light. Numerous papers have been written and experiments conducted showing how polarized light interacts with such structures. See, e.g., S. P. Morgan and I. M. Stockford, "Surface-reflection elimination in polarization imaging of superficial tissue," Opt. Let. 28, 114-116 (2003), incorporated herein by reference. Much of this work has been done to exploit the use of polarized light to reduce the image degrading effects of scattering particles while looking at objects of interest at some depth into the tissue. The path length distribution of detected light through the tissue will be affected by the polarization states of the illuminating and collected light.

A matrix representation of the way a medium changes the polarization properties can be used in measuring and analyzing polarized light, e.g., the Mueller matrix, a square matrix containing 16 elements. The Stokes vector can be used to describe the state of polarization of the illuminating and collected light. See, e.g., C. Bohren and D. Huffman, Absorption and Scattering of Light by Small Particles (John Wiley & Sons, New York, 1983), pp 41-56, incorporated herein by reference. It can be derived from four independent polarization states, such as vertical linear polarization, horizontal linear polarization, +45 degree linear polarization, and left circular polarization. By illuminating the medium with each of these states and then, at each illumination state, observing the response using an analyzer set to each of these states, a set of 16 independent states can be observed (4 collection states for each of 4 illumination states), making up the elements of the Mueller matrix. Multiplying the input Stokes vector by the Mueller matrix produces the output Stokes vector. Although determining a complete Mueller matrix for individual tissue samples might be useful for characterizing differences between people, it is not necessary to do so to obtain useful information. Measurements using only a few polarizer positions can provide insight into the way one tissue sample scatters light differently than another tissue sample, allowing an improved calibration model to be constructed that takes advantage of this knowledge.

Figure 5:
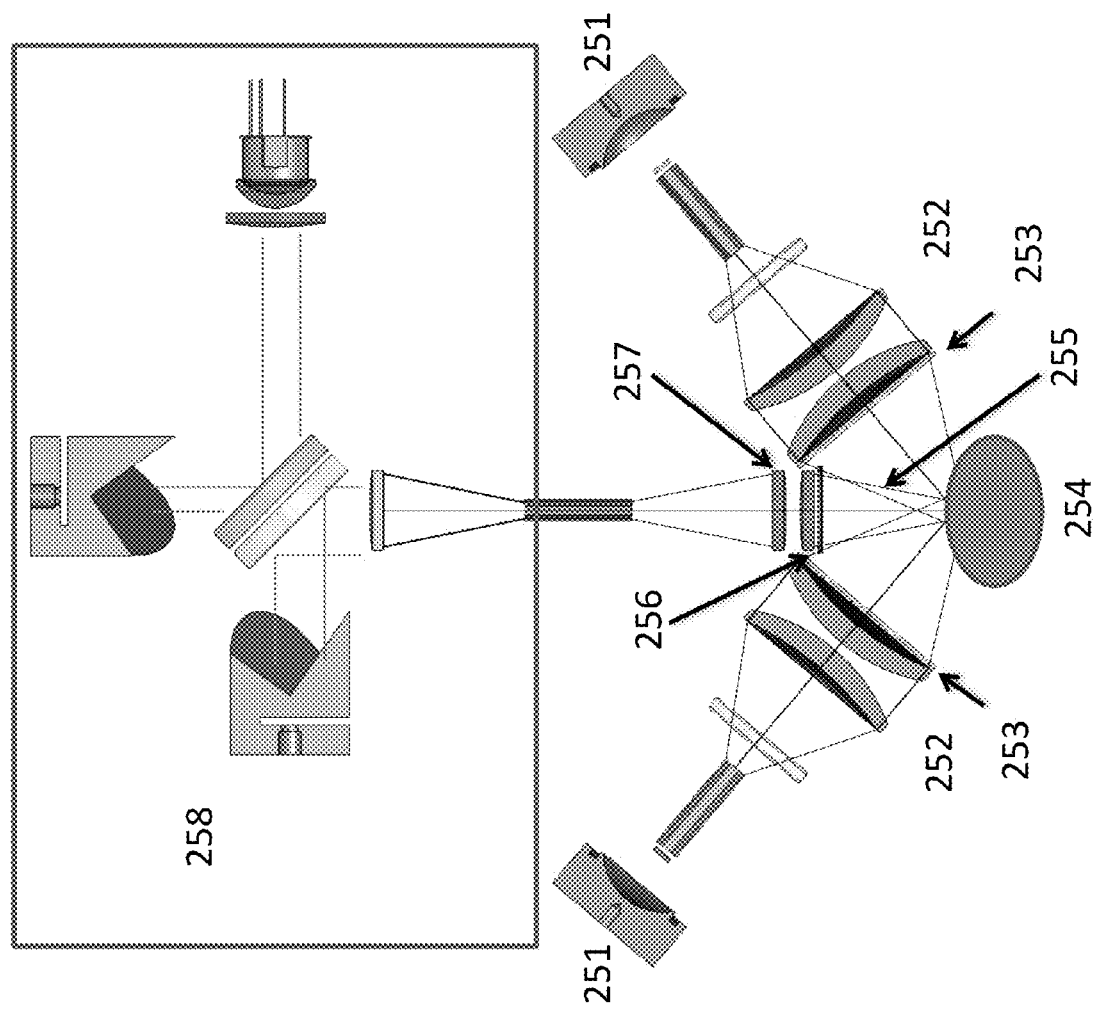
FIG. 5 is a schematic illustration of a system for noninvasive glucose monitoring according to the present invention.

FIG. 5 illustrates an example embodiment of a system for noninvasive glucose monitoring. Two light sources 251 can be used to reduce source fluctuation. The light for the source is collected and relayed by optics 252. The light is transmitted through illumination polarizer 253, to the tissue, e.g., a finger 254 as shown. The input light, containing multiple wavelengths, is diffusely scattered by the tissue, with a portion of the light being returned back. The returning light contains photons whose polarization has not been altered as well as photons whose polarization has been changed through a scattering event. Light maintaining the polarization of the input polarizer is referred to as $I_{par}$ and photons whose polarization has been altered are referred to as $I_{per}$. The $I_{par}$ consists of the superficially reflected light ($R_s$) plus one half of the deeply penetrating light (Rd). The term "deeply penetrating" refers to light that has penetrated the tissue and experienced a scattering event that has altered the original polarization. The light returned from the tissue 255 contains both polarization states. Polarizer 256 can be rotated so as to preferentially select those photons maintaining the input polarization or for those photons whose polarization has been modified. The angle between the illumination and collection polarizer can be varied to any desired angle but for the preferential selection of glucose containing photons a 90° angle is used. Collection optics 257 collects the light satisfying the polarizer orientation and relays the light into the Fourier transform infrared spectrophotometer 258. For illustration purposes the Fourier transform infrared spectrophotometer shown is a Michelson interferometer.

Figure 6:
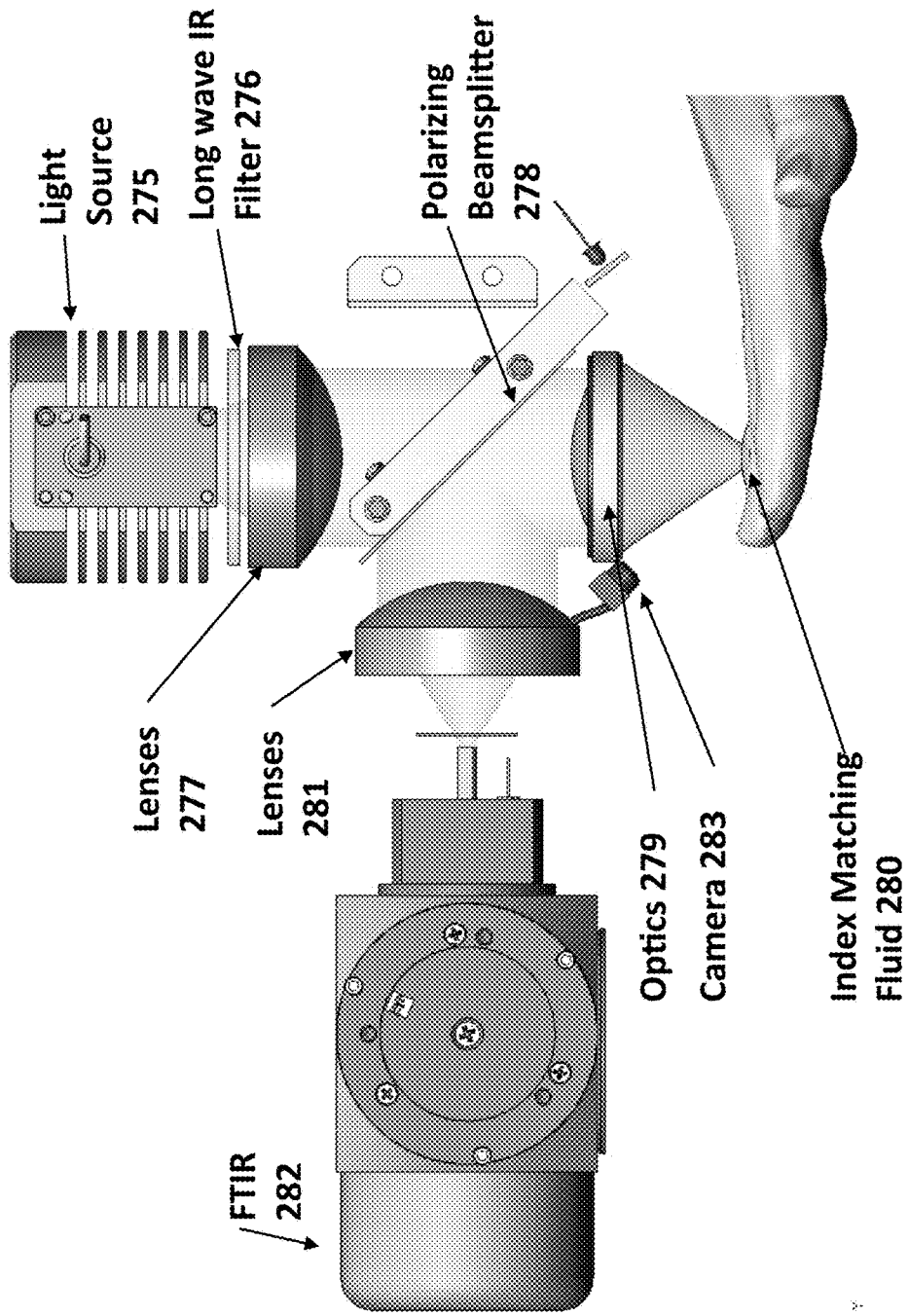
FIG. 6 is a schematic illustration of a system for noninvasive glucose monitoring according to the present invention using a collinear sampling geometry.

FIG. 6 illustrates an example embodiment of a noninvasive measurement system that satisfies the stringent requirements of a noninvasive glucose monitoring system. The configuration of the system differs from other described embodiments in that a polarizing beam splitter is utilized to separate parallel polarized light from perpendicularly polarized light. Light source 275 generates multiple wavelengths of near infrared light. These wavelengths of light are selected for the region of interest by long wave IR filter 276. The light is subsequently collimated by optics 277 onto polarizing beam splitter 278. The light satisfying polarization requirements defined by the beam splitter is subsequently communicated to focusing optics 279. The illumination photons subsequently interact with the tissue (back of finger shown). The enclosed figure also depicts the use of an index matching fluid 280 placed on the back of the finger to further facilitate specular/glare/short path photon rejection. The diffusely reflected light is then re-collected by optics 279 for interaction with beam splitter 278. Those photons whose polarization is perpendicular to the input polarization are reflected to lenses 281. Lenses 281 subsequently focus the light into Fourier Transform Infrared Spectrophotometer 282. Also shown in FIG. 6 is an alignment mechanism to ensure the repositioning of the finger in an appropriate location. Camera 283 can ensure the appropriate alignment of the finger based upon a number of geometries present on the hand.

The specific embodiments defined above satisfy the stringent requirements associated with measuring glucose noninvasively. Specifically, the systems enable the measurement of measurement of multiple wavelengths (greater than 12) with high signal-to-noise while not burning the tissue. This objective is satisfied by utilizing high throughput optical measurement system that leverages Fellgett's advantage or Jacquinot's advantage or both. The instrumentation enables the simultaneous measurement of multiple wavelengths of light resulting in an appropriate/reasonable measurement period. The use of polarization as a photon selection methodology for those photons containing glucose information while not compressing the tissue with a contact based probe creates a tissue sampling methodology that provides repeatable sampling and where the tissue is not mechanically altered by the sampling process.

Figure 7:
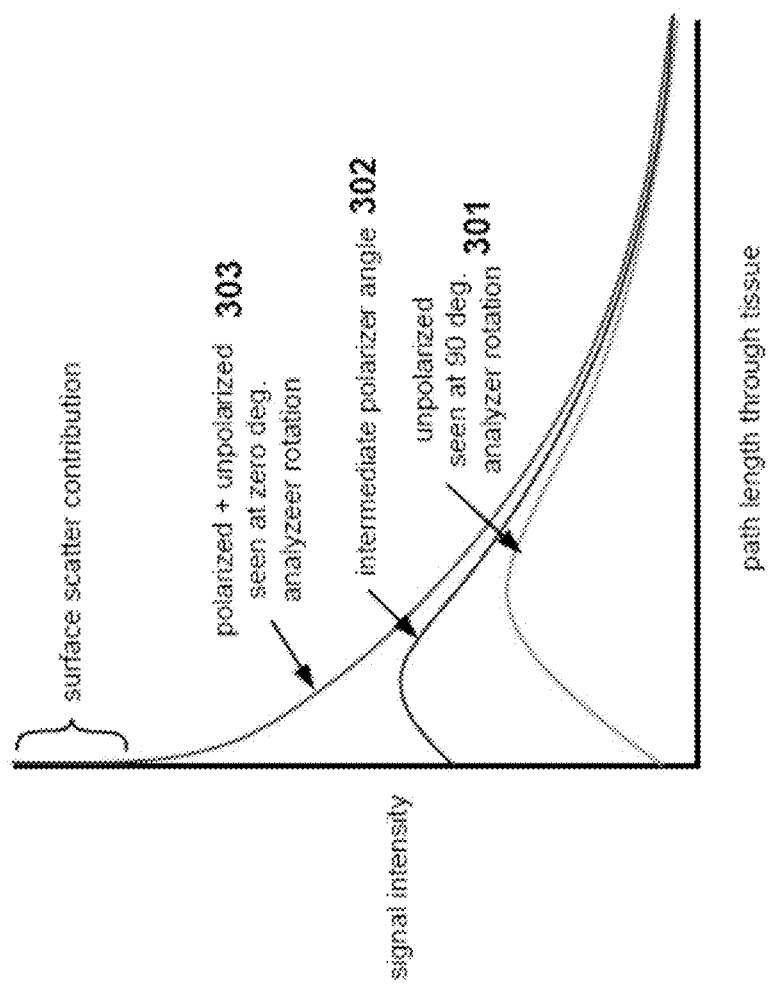
FIG. 7 is a conceptual illustration of signal intensity vs. optical path length of light back scattered from a bulk scattering medium.

FIG. 7 is a conceptual illustration of signal intensity vs. optical path length of light back scattered from a bulk scattering medium, roughly representative of the properties of human tissue, for each of several path length distribution. Because tissue is a scattering medium, light entering the tissue from the spectrometer must generally undergo one or more scattering events to reverse direction and exit the tissue to be collected by the detector. When polarized light undergoes a scattering event it becomes partially depolarized, i.e. a portion of the light can become randomly polarized while another portion of the light might maintains its original state of polarization. The amount of depolarization the light will undergo at each scattering event can depend on a number of parameters including the particle refractive index, shape, size and the scattering angle. These properties can vary from person to person and with the physiological state of the person, such as age or level of hydration. In general, the longer the path length of the light in the tissue the more scattering events it will encounter and the more random its polarization will become. Additionally, the depth of penetration will typically be greater as the path length increases as a function of the amount of cross polarization. Thus, light scattered from regions near the surface or traveling short path lengths will generally maintain a larger fraction of its original polarization state than light penetrating deeper into the tissue and traveling a longer path. Light penetrating deeper into the tissue will also be more heavily attenuated by absorption in the tissue and scatter out of the detector field of view, so the total intensity of long path length light will be reduced regardless of polarization state.

FIG. 7 shows the expected path length distribution for several orientations of an analyzer. When the analyzer is rotated so that its polarization axis is at a 90 degree angle to the input polarizer the light maintaining its original polarization is attenuated by the maximum amount, allowing only crossed or randomly polarized light to pass 301. Light traveling a more direct short path, having maintained more of its original polarization state, is attenuated more than light traveling a longer path. When the analyzer is oriented with its polarization axis parallel to the input polarizer axis 303 both the linearly polarized and randomly polarized light satisfying the orientation requirements of the collection polarizer can pass. In this orientation a larger portion of the shorter path light will be detected, having undergone fewer scattering events. At intermediate orientations 302 of the analyzer the change in weighting of the shorter and longer path length light in the composite signal will produce a distribution weighted more towards shorter path lengths than that of the crossed polarizer position.

The example embodiment represents a major advancement in tissue sampling: a sampler that samples a relatively large area, without requiring contact with the tissue, with strong specular rejection capabilities, and the ability to generate multi-path data by changing the state of polarization between the illumination and collection optics.

Additional Embodiments and Improvements

A sampling system such as described in the example embodiment above can be modified for specific performance objectives by one or more of the additional embodiments and improvements described below.

Auto Focus.

A motorized servo system along with a focus sensor, such as that used in autofocus cameras, can be used to maintain a precise distance between the tissue and the spectral measurement optical system during the measurement period. The tissue, the optical system, or both can be moved responsive to information from an autofocus sensor to cause a predetermined distance between the tissue and the optical system. Such an autofocus system can be especially applicable if the sampling site is the back of the hand or the area between the thumb and first finger. For example if a hand is placed on a flat surface, the auto focus mechanism could compensate for differences in hand thickness.

Tissue Scanning.

The tissue can be scanned during a measurement to create an extremely large sampling area. The scanning process can involve scanning a tissue site by moving the tissue site relative to the sampler, or by moving the sampler relative to the tissue site, or by optically steering the light, or a combination thereof.

Location Feedback on Tissue Surface.

The measurement system can inform the user if the tissue site is inserted into the correct focal plane or location. Many optical location or measurement systems exist, such as those commonly used for the determination of interior wall dimensions. Such a system can provide information of the general location of the tissue plane as well as the tilt of the tissue plane.

Use of Different Input Polarization States.

Because of anisotropy in the structure of the tissue, e.g., anisotropy due to collagen strands, uniquely different path length distributions can be obtained by collecting data at different illumination polarizer angles. These changes in input polarization angle coupled with concurrent changes in collection polarization angle can provide a diversity of pathlength observations.

Use of Different Types of Polarization.

Circular and linearly polarized light can behave differently. The use of different types of polarization can be used to enhance pathlength differences. Circularly polarized light can maintain a larger portion of its original polarization state with each forward scattering event. Thus, the use of different types of polarization can be used for the generation of different pathlength data.

Use of Different Collection and Illumination Angles.

The angles of the illumination optics and collection optics relative to each other and relative to the tissue surface can influence the path length distribution. As described above, the illumination and collection optics are arranged to avoid the collection of direct specular reflection from the tissue surface. Depending upon the relationship between the illumination and collection optics, the system can be configured such that the collected light must undergo the required polarization changes and required changes in direction. Generally, greater required change of direction means longer pathlength in the tissue.

Separation of Illumination Area and Collection Area.

The amount of specular light can be further reduced by separating the illumination and collection areas. As illustrated in FIGS. 5 and 6, the illumination area (also known as the illumination focal plan) is centered about the same point as the collection area (also known as the collection focal plan). The resulting system uses concentrically based illumination and collection areas. The optical system can be designed so that non-concentric illumination and collection areas are used. A the extreme, the collection and illumination areas are completely separate. Separated illumination and collection areas require the light collected by the system to propagate horizontally, typically in the tissue, prior to collection by the collection system. The requirement of tissue propagation generally increases as center of the illumination and collection systems increase. The separation of illumination and collection areas can be used to guarantee a minimal path through tissue Reduction of Skin Surface Artifacts.

Tissue surface roughness can cause polarization changes that are unrelated to changes in polarization state due to propagation through tissue. The potential problem can be mitigated by coating the tissue surface with a fluid having no or few interfering absorbance features in the spectral region of interest. The use of such a skin smoothing fluid reduces polarization changes due to surface roughness. An oil with few absorbance features is Fluorolube, a fluorinated hydrocarbon oil. A light coating with such a smoothing agent can reduce the signal produced by surface scatter with minimal disturbance of the observed tissue spectra. The proper application of the smoothing agent (e.g., presence, thickness, material) can be determined from spectral features distinguishable as properties of the agent. For example, additives with known absorbance properties can be added to Fluorolube, and the spectroscopic system can determine the characteristics of the Fluorolube agent from observation of those properties. Additionally, the removal or minimization of hair can reduce artifacts due to tissue roughness.

Sampling of the Same Tissue Volume.

Due to the heterogeneous nature of tissue, it is desirous to sample the same tissue location or tissue volume. Several patent applications or patents have sought to address this problem by using an adhesive to temporarily attach various mechanical devices to the arm, such as a metal plate or EKG probes. See, e.g., U.S. Pat. No. 6,415,167, incorporated herein by reference. The arm is then placed on the sampler using these devices to position the arm into a mating receptacle. These devices are, at best, a very temporary means of helping to repeatedly relocate the arm during a short set of measurements. They cannot be used as a permanent fiducial to reduce measurement error over a long period of time.

Two or more ink spots on the arm outside the measurement region have been demonstrated in our laboratory to be useful in guiding positioning of the tissue. A TV camera looking at the arm from the sampler side can be used to visually guide placement of the arm onto the sampler, allowing the person being measured or an assistant to move the arm around until the ink spots are aligned with spots placed on the screen of the TV monitor. This scheme can be used over a long term by permanently tattooing the marks into the skin. Users have generally deemed this unacceptable. It also precludes easily changing measurement locations should a given sampling area become desirable.

Vein or capillary imaging can be used instead of ink spots or tattoos to provide lasting reference marks for positioning of the tissue. Vein or capillary imaging can use an optical illumination and image capture method to make veins or capillaries near the tissue surface visible, for example, on a TV monitor. In practice for analyte measurements, a measurement site can originally be located according to criteria dictated by an end application, such as non-invasive blood glucose measurement. A vein or capillary image can then be recorded either coincident with the measurement site or from surrounding regions. This recorded image can then be used as a template to guide relative placement of the tissue and sampling system in future measurements. It can be used as a visual aid to manually place the tissue in the correct location or it can be used in a servomechanism using image correlation to automatically place and maintain the instrument or tissue in the correct location. An automated system might be especially useful in maintaining position when there is no direct physical contact between the measurement apparatus and the tissue at the measurement location.

Methods of vein imaging have been described in the literature for other applications including biometric identification and assistance devices for blood withdrawal. Vein imaging techniques generally seek to obtain maximum contrast between veins and surrounding tissue. In one described technique, polarized light at 548 nm was used to illuminate the tissue in a small region. See, e.g., http://oemagazine.com/fromTheMagazine/nov03/vein.html, visited Jan. 15, 2006; U.S. Pat. No. 5,974,338, "Non-invasive blood analyzer," issued Oct. 26, 1999, each of which is incorporated herein by reference. As the light penetrates the tissue it is scattered, illuminating a larger volume of the tissue. Light back scattered from shallow regions maintains some of its original polarization and thus can be attenuated by a crossed polarizer on the video camera. Light penetrating deeper loses its polarization and is detected by the camera, effectively back illuminating veins in the path. At a selected wavelength, blood has an absorption peak allowing a vein to be seen as a dark object against the brighter background of light scattered from underlying tissue. In other references polarized light from LEDs at 880 nm or at 740 nm are used to flood illuminate the tissue and again a crossed polarizer on a CCD camera helps to reject surface reflections and shallow depth scattered light. See, e.g., http://www.news-medical.net/?id=5395; http://www.luminetx.com/home.html; http://www.nae.edu/NAE/pubundcom.nsf/weblinks/CGOZ-65RKKV/$file/EMBS2004e.pdf, all visited Jan. 15, 2006. At these longer wavelengths the tissue scattering is less than at the shorter wavelength of 548 nm so the light can penetrate a larger distance, allowing deeper veins to be observed. Absorbance of blood at 880 nm is much less than at 548 nm so computer processed contrast enhancement may be needed to clarify the vein images. Other techniques involve injecting a contrast enhancing dye into the blood stream, which might not be acceptable for many analyte measurement applications.

Additional Capabilities

Removal of Surface Contaminants.

Light scattering by tissue gradually randomizes the original polarization state of the illuminating light. Unscattered or weekly scattered light maintains its polarization state, whereas multiple-scattered light is randomly polarized and contributes equally to both copolarization and cross polarization states. Simple subtraction of the two states enables the weakly scattering component to be reduced See, e.g., Morgan, Stephen et al, Surface-reflection elimination in polarization imaging of superficial tissue, Optics Letters Vol 28, No 2, Jan. 15, 2003, incorporated herein by reference. Thus, surface contamination issues such as powered sugar for glucose measurements or liquor on the surface of the arm for noninvasive alcohol measurements can be largely eliminated by effectively processing data from different polarization states.

Processing of the Spectra for Minimization of PLD Differences.

Information from multiple path lengths can be used to explicitly define or resolve the PLD. Another, simpler approach uses the different pathlength data to minimize the differences in the PLD and to create a PLD with the narrowest possible distribution. Suppose that the scattering resulted in photons taking one of two possible pathlengths, $l_1=1$ and $l_2=3$ (each with 50% likelihood), then the resulting measured transmission or absorbance is $$R_1 = \frac{I_\lambda}{I_{\lambda,o}} = (0.5) \cdot 10^{-(\varepsilon_\lambda l_1 c)} + (0.5) \cdot 10^{-(\varepsilon_\lambda l_2 c)}$$

$$a_\lambda = -\log_{10}((0.5)10^{-(\varepsilon_\lambda l_1 c)} + (0.5)10^{-(\varepsilon_\lambda l_2 c)})$$

This result is unfortunately not linear with respect to concentration. Suppose, however that the optical sampling mechanism can measure the $l_2=3$ pathlength in isolation. Its reflectance is simply $$R_2 = \frac{I_\lambda}{I_{\lambda,o}} = (1) \cdot 10^{-(\varepsilon_\lambda l_2 c)}$$

or $$\frac{1}{2} \cdot R_2 = (0.5) \cdot 10^{-(\varepsilon_\lambda l_2 c)}$$

In this trivial case, subtracting eq. 4 from eq. 1 gives a differential reflectance $$R_\Delta = R_1 - \frac{1}{2}R_2$$
$$= [(0.5) \cdot 10^{-(\varepsilon_\lambda l_1 c)} + (0.5) \cdot 10^{-(\varepsilon_\lambda l_2 c)}] -$$
$$[(0.5) \cdot 10^{-(\varepsilon_\lambda l_2 c)}]$$
$$= (0.5) \cdot 10^{-(\varepsilon_\lambda l_1 c)}$$

And $R_D$ actually has a discrete pathlength of $l_1$. This simple example can be extended to situations where two or more distinct path lengths are generated, as shown in FIG. 6. These spectra can be processed by multiple methodologies to include simple subtraction to create a narrower 'differential path length distribution'. The results can be a 'mix-and-match' differenced/integrated spectrum that has a narrower pathlength distribution than any of the individual channels of data. It is recognized that an important assumption for this technique is that the chemistry at the different path lengths is fixed. Specifically, the previous equation assumes that 'c' must be common to both $R_1$ and $R_2$. Although the composition of the tissue is not necessarily fixed across widely varying pathlengths, the normalization of PLD in this manner has been shown to be beneficial. Also, a narrower PLD can be desirable since it is closer to a single pathlength, and thus closer to the assumption behind Beer's law.

Use of Different Spectral Resolutions.

Spectral data from the front surface of the tissue often contains little useful analyte information. As shown in FIG. 5, a sampling configuration where the illumination and collection polarization angles are the same generates date that contains a significant amount of signal from zero or very short path length light. This is light scattered from the surface and from very shallow depths where the analyte concentration is typically very low and thus is different from the systemic analyte concentration or the deeper tissue. The collected data can be de-resolved relative to the resolution of the collected spectra. The process of de-resolving the data can effectively diminish the influence of the analyte concentration on the data while maintaining general information associated with the tissue, such as tissue reflectance, tissue location, tissue smoothness, etc. Since the surface and shallow layer scattered light contains little or no absorbance features associated with the analytes of interest a spectral reflectance measurement made at low spectral resolution can be subtracted from the higher resolution spectrum without losing the desired spectral absorbance features from deeper in the tissue. Experimental or theoretical methods can be used to determine the optimum spectral resolution for this "background" light and different combinations of data at different polarizations can be used with this processing method.

Adaptive Sampling.

Experimental studies as well as simulation studies have shown that the parameters of the optical sampler can influence the PLD obtained. Specifically, the PLD obtained can be influenced by the configuration of the sampler. Important parameters include the numerical aperture of the input and output optics, the launch and collection angles, the separation between the input and output optics, and the polarization (linear or circular) of the input and output optics. The optical system can be adjusted real-time to generate the desired PLD. The adjustment of these parameters alone or in combination allows the system to procure a single spectrum with the most desirous PLD.

Direction of Change Measurements.

In the management of diabetes, the individual with diabetes typically receives a point measurement associated with the current glucose level. This information is very useful but the value of the information can be dramatically enhanced by the concurrent display of the direction of change. It has been desired that the measurement device report the glucose concentration, the rate of change, and the direction of change. Such additional information can lead to improved glucose control and greater avoidance of both hypoglycemic and hyperglycemic conditions. Such a measurement has not been possible with current contact samplers because the tissue becomes compressed during the measurement process. Thus, the path length distribution changes and the highly precise measurement need for direction of change can not be obtained. With a non-contact sampler like that described herein, the tissue is not compressed and the sampling surface does not change due to contact with the sampler, allowing determination of the direction of change of the analyte concentration. See, e.g., U.S. patent application Ser. No. 10/753,50, "Non-Invasive Determination of Direction And Rate Of Change of an Analyte," incorporated herein by reference.

Additional Sampler Embodiments

Various additional example embodiments are described to help illustrate advantages possible with the present invention. The example embodiments are illustrative only; those skilled in the art will appreciate other arrangements and combinations of features.

Example Embodiment

The sampler discussed above uses the changes the amount of cross polarization between the illumination and collection optics to measure light that has traveled at two or more different path length distributions. The spatial spread of the light can also be used to generate path length differences in the collected spectra. If the tissue is illuminated by a point source and the diffusely reflected light is received by a collection point, the path length distribution can change as the collection point is moved to different distances from the illumination point. The rate of falloff of the light intensity with distance from the origin will be dependent on the scattering and absorption properties of the tissue. The samplers described in the following text take advantage of this phenomenon.

In an example embodiment incorporating this feature, a variable path sampler uses light from a small source focused onto the tissue by a lens or mirror. A second lens or mirror collects light from a point on the tissue and focuses it onto a detector. Although, in principle, the same lens or mirror can be used for both illumination and collection, it can be advantageous to use separate optical components. This allows for the placement of baffles to help in eliminating collection of light scattered directly from the source-illuminated optics (i.e., without interacting with a sufficient depth of tissue). A spectrometer can be placed either in the path from the source to the tissue or in the path from the tissue to the detector. The physical separation between the illumination and collection spots on the tissue determines the shortest possible path length of light traveling through the tissue. To obtain different path length distributions, data can be collected with different physical separations between the input and output optics.

Figure 9:
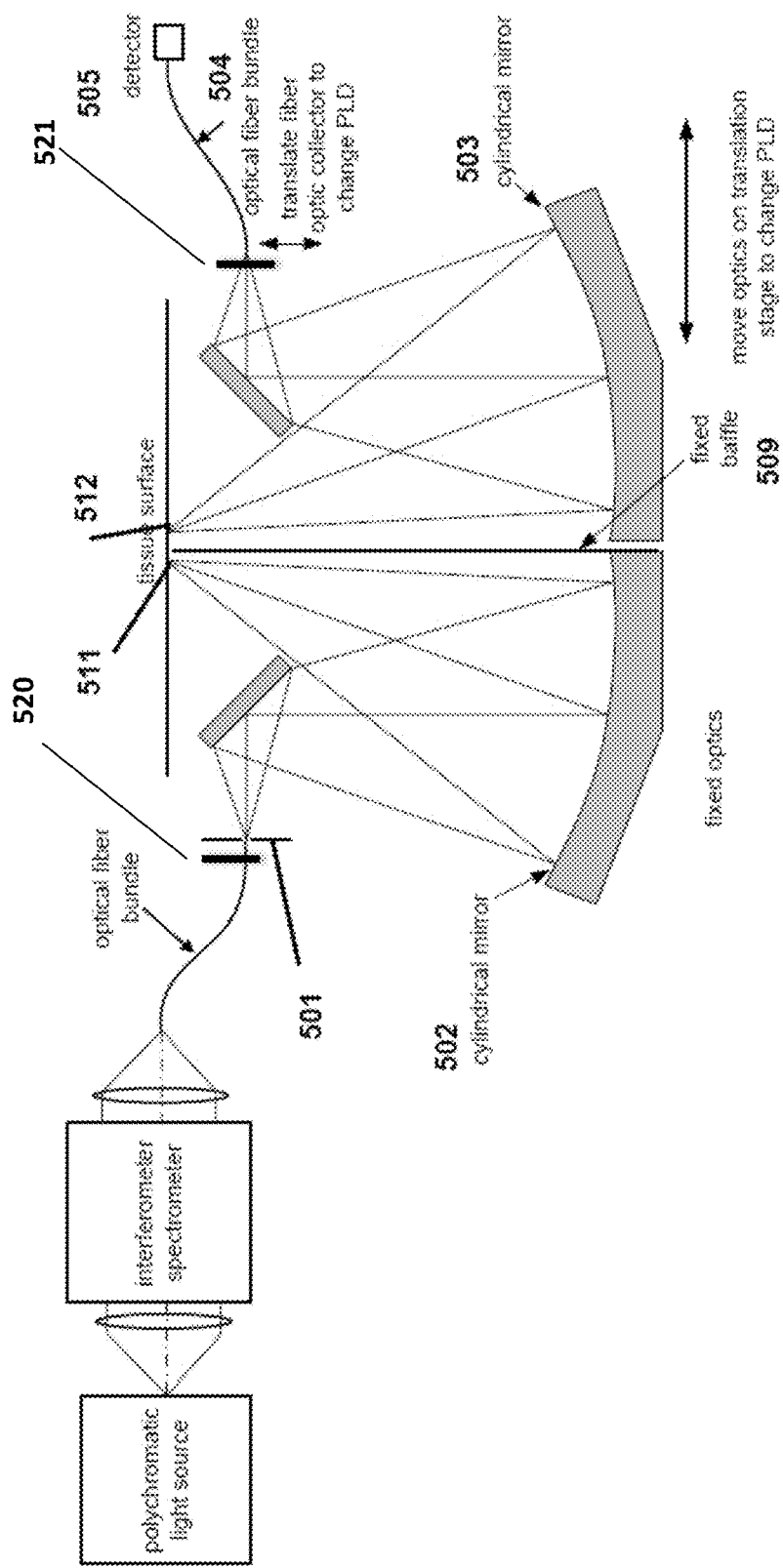
FIG. 9 is a schematic depiction of an example embodiment.

In practice the input and output need not be limited to single points. FIG. 9 is a schematic depiction of an example embodiment. A narrow slit-shaped light source 501 can be formed from a fiber optic circle-to-line converter. A cylindrical mirror 502 can image a line 511 of light onto the tissue 508. Another cylindrical mirror 503 can collect light from a line 512 on the tissue surface 508 and image it onto a row of optical fibers 504 that can be configured into a circular bundle for more efficient coupling to a detector 505. The two image lines 511, 512 can be aligned parallel to but offset from each other. Varying the distance between the two lines 511, 512 can vary the minimum optical path length through the tissue. The distance can be varied in several ways. As one example, the optics to the right side of the baffle 509 can be mounted on a translation stage and moved horizontally to vary the position on the tissue of the pickup point or line. Alternatively, either the fiber optic source or pickup bundle, alone, can be translated along the plane of best focus (approximately vertically). The system can contain polarizers 520 and 521 on the illumination and collection systems. The resulting system has a very strong method for excluding front surface reflected photons by using both cross polarization as well as separation of the illumination and collection areas.

This example sampler has numerous advantages: no mandatory contact with tissue in measurement region; surface scattered light can be rejected through baffling and the imaging properties of the optical system; and path length distribution, especially the minimum path, can be easily changed by changing the physical separation between input and output spots or lines. In some applications, it can be important to position the tissue accurately to maintain the lines in sharp focus.

Example Embodiment

Figure 8:
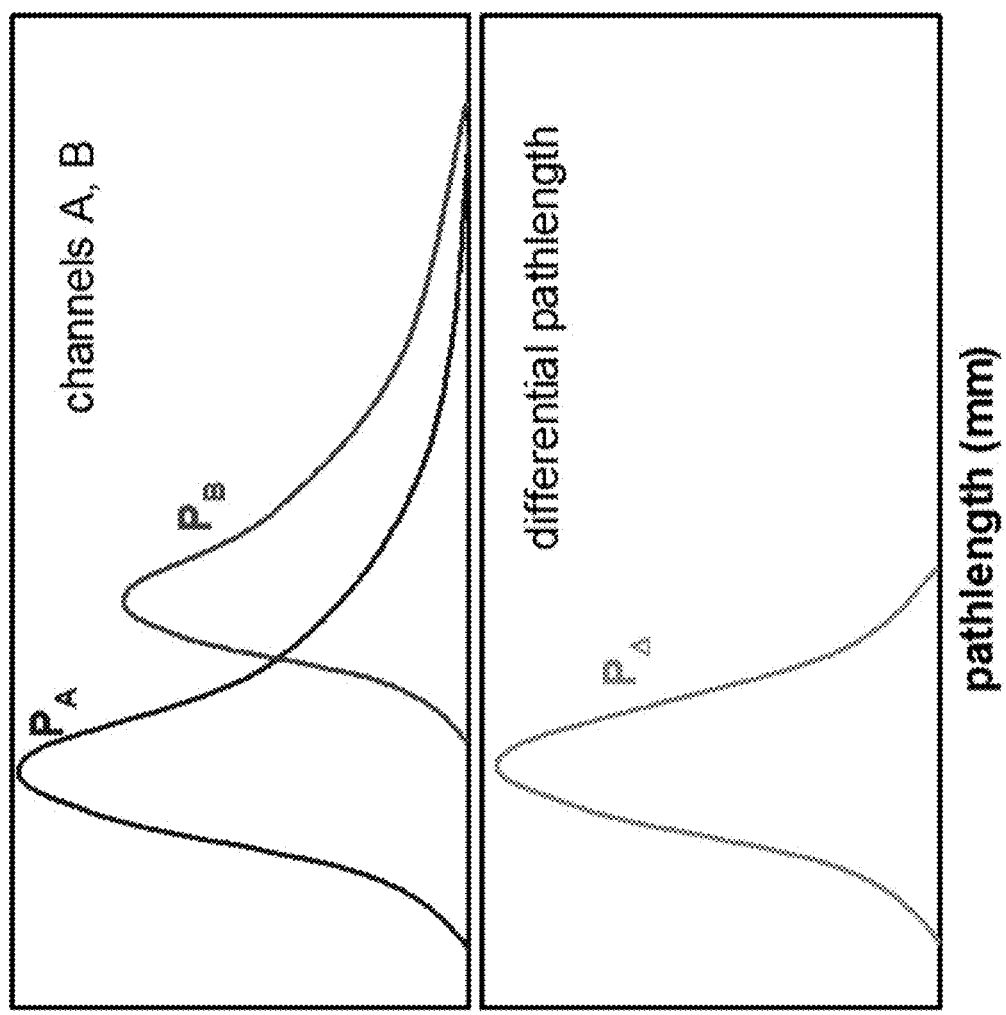
FIG. 8 is a schematic illustration of a situation with two or more distinct path lengths.
Figure 10:
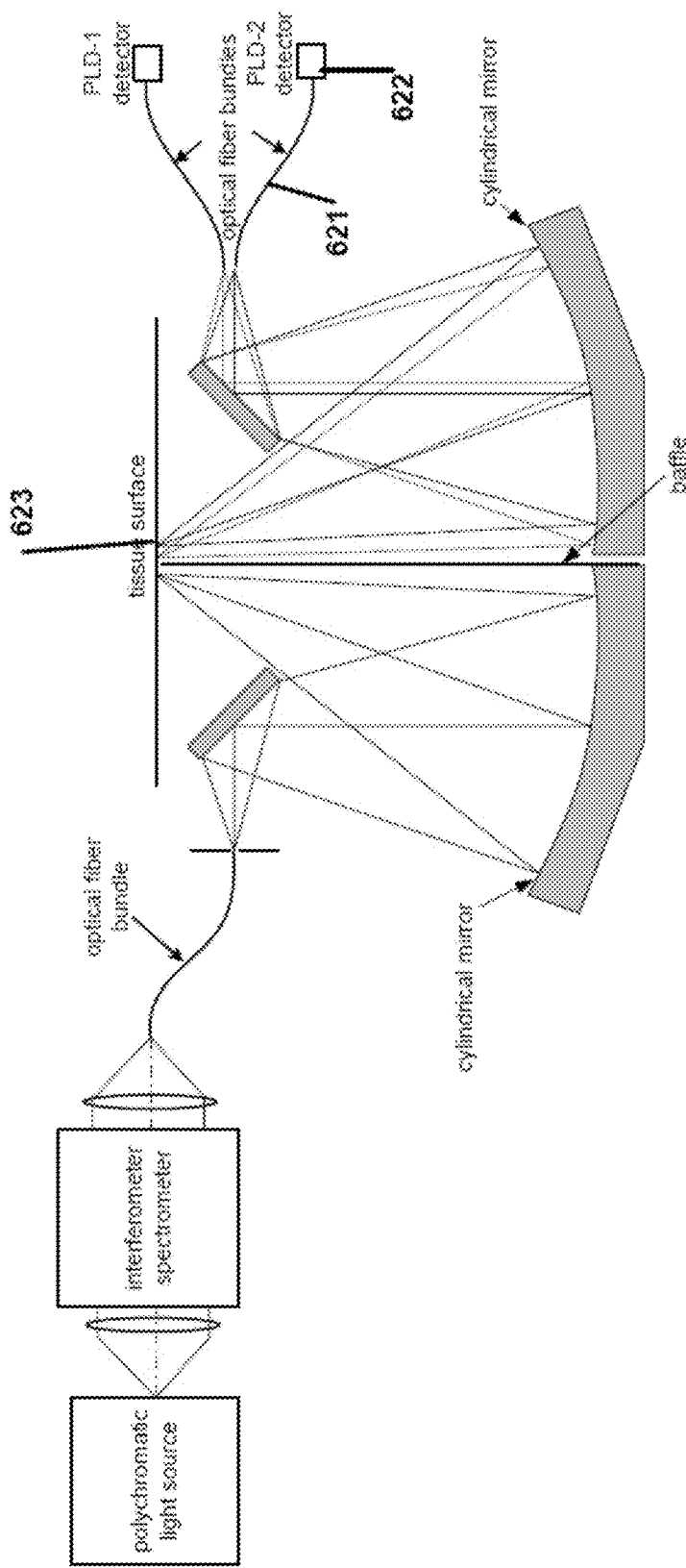
FIG. 10 is a schematic depiction of an example embodiment.

FIG. 10 is a schematic depiction of another example embodiment. This example embodiment has similar components and arrangement as the previous example. A second row of collection fibers 621 collects light from a second collection line 623, allowing simultaneous collection of light from two different path length distributions. Simultaneous collection can reduce errors due to temporal changes. Two or more simultaneous collection lines can be combined with translation as in the previous example to allow different pairs of areas to be interrogated. Polarization of the illumination and collection light can also occur in a manner similar that that shown in FIG. 8.

Another variation of this example embodiment illuminates an annular ring mask and focuses an image of the ring onto the tissue. Light is then collected from a small point in the center of the ring and focused onto the detector. By changing the annular ring mask a series of different separations between source and collector can be achieved. This embodiment can be extended with an optical system that focuses multiple images of the annular ring onto the tissue and collects light from multiple centered points onto a detector.

Any of the examples embodiments can be used with or without a sample positioning window or index matching fluid in contact with the tissue. They can also be used with the spectrometer either in the path before or after the tissue.

Example Embodiment

Figure 11:
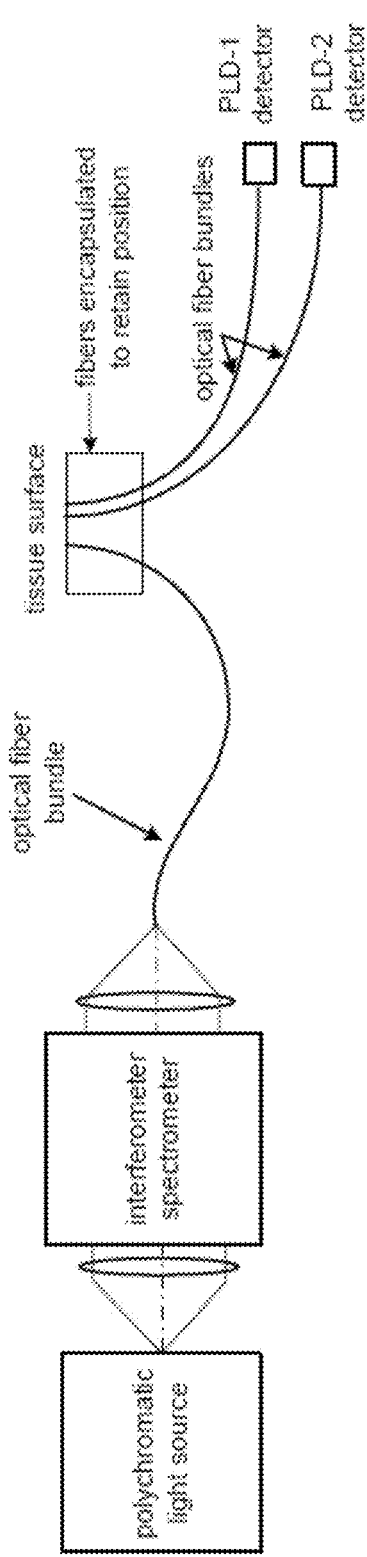
FIG. 11 is a schematic depiction of an example embodiment.

FIG. 11 is a schematic depiction of an example embodiment. This sampler eliminates the re-imaging optics of the previous sampler, bringing the light to and from the tissue by directly contacting optical fibers with the tissue. This arrangement can reduce the requirement for precision optical alignment to that required in the permanent placement of the fibers during manufacture. Physical contact can also help reduce the collection of light scattered from the tissue surface. Direct tissue contact, however, can produce tissue property changes due to interface moisture changes and compression of the underlying structure.

Experimental Results

A series of tests were conducted with the various tissue sampling embodiments previously discussed with a goal of demonstrating and measuring their improved performance. These experiments involved both a tissue phantom model composed of scattering beads and tests on human tissue.

The tissue phantoms were sampled in a back scattering mode or via diffuse reflectance similar to the way the samplers would be used to measure human tissue. The tissue phantoms consisted of water solutions in a container with a flat transparent window. Various concentrations of several analytes, such as glucose and urea were included at concentration ranges found in human tissue. A range of concentrations of suspended polystyrene beads was also included to vary the scattering level and thereby the path length distribution of light propagating through the solution. The set used for testing was composed of 9 different scattering concentrations from 4000 mg/dl to 8000 mg/dl. See, e.g., U.S. patent application Ser. No. 10/281,576, "Optically similar reference samples," filed Oct. 28, 2002, incorporated herein by reference. This variance in scatter results in a path length variation of approximately ±25%. Spectral response data were then collected using a sampler like that described in connection with FIG. 4, configured with a polarizer and analyzer but without quarter wave plates. Data were collected for each sample using different amounts of cross polarization.

Human testing was also conducted with the same optical system. The arm was inserted by placing the elbow on an elbow cup and the subject's hand gripping or placed against a vertical post. The palm of the patient was perpendicular to the ground. No window or other locating device was used to control the subject's arm position.

Large Area Sampled.

Figure 12:
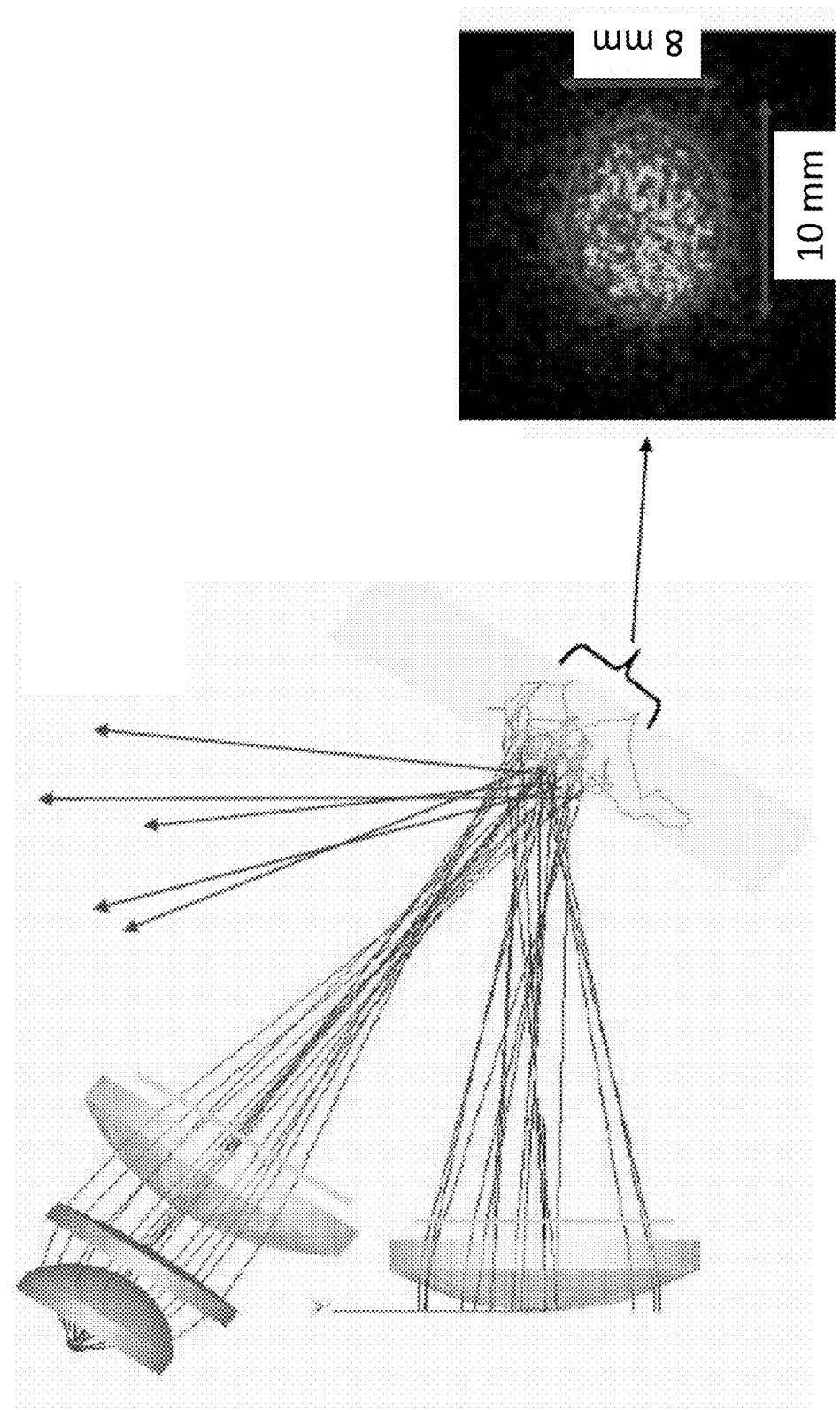
FIG. 12 is a schematic illustration of the flood illumination area of an optical sampler.

As shown in FIG. 12, the optical system flood illuminates a sampling area with an oval spot that is greater than 8 mm in diameter. The area sampled is about 12.5 times larger than that sampled with previous fiber optic samplers.

Similar Information Content of Spectra.

Figure 13:
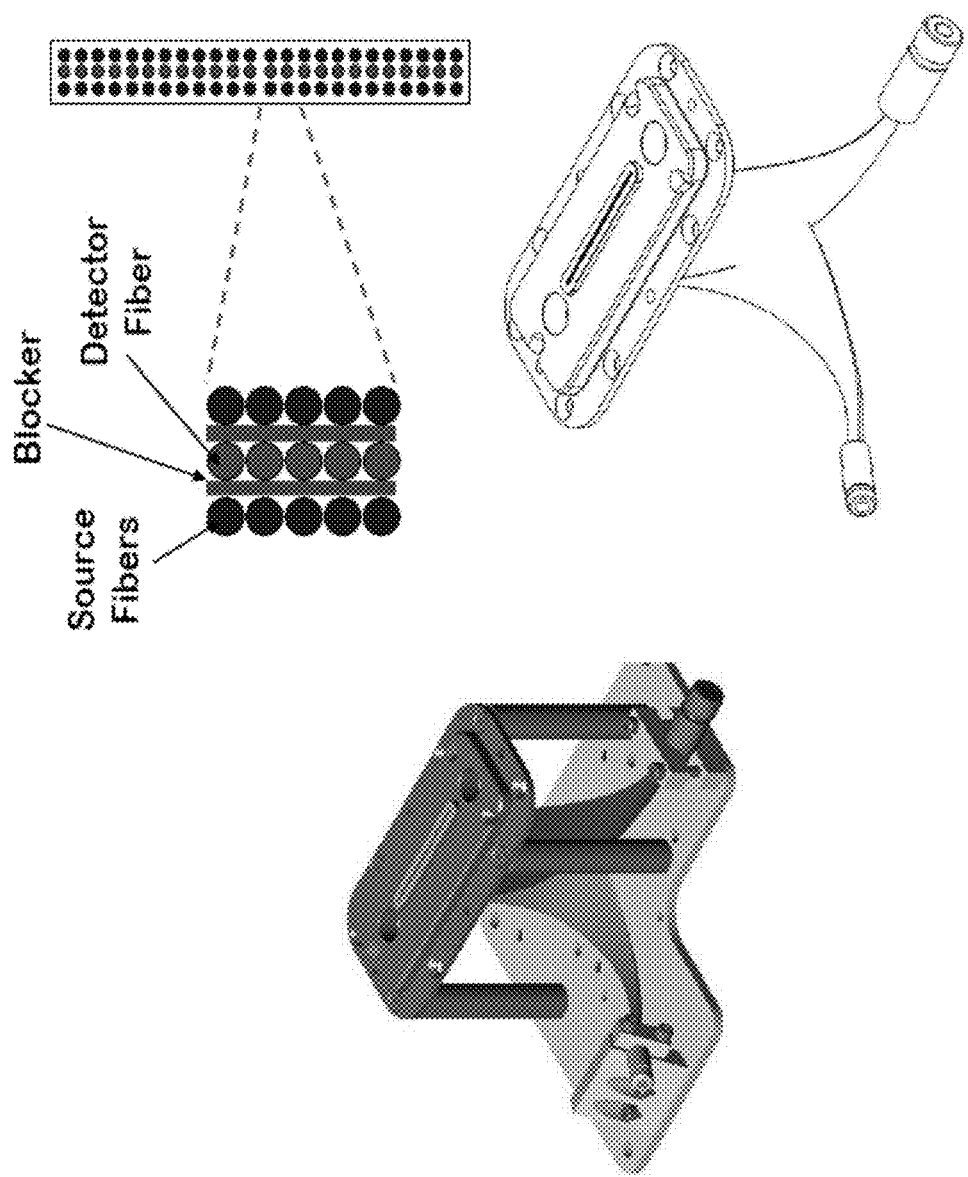
FIG. 13 is a schematic illustration of a fiber based sampler.
Figure 14:
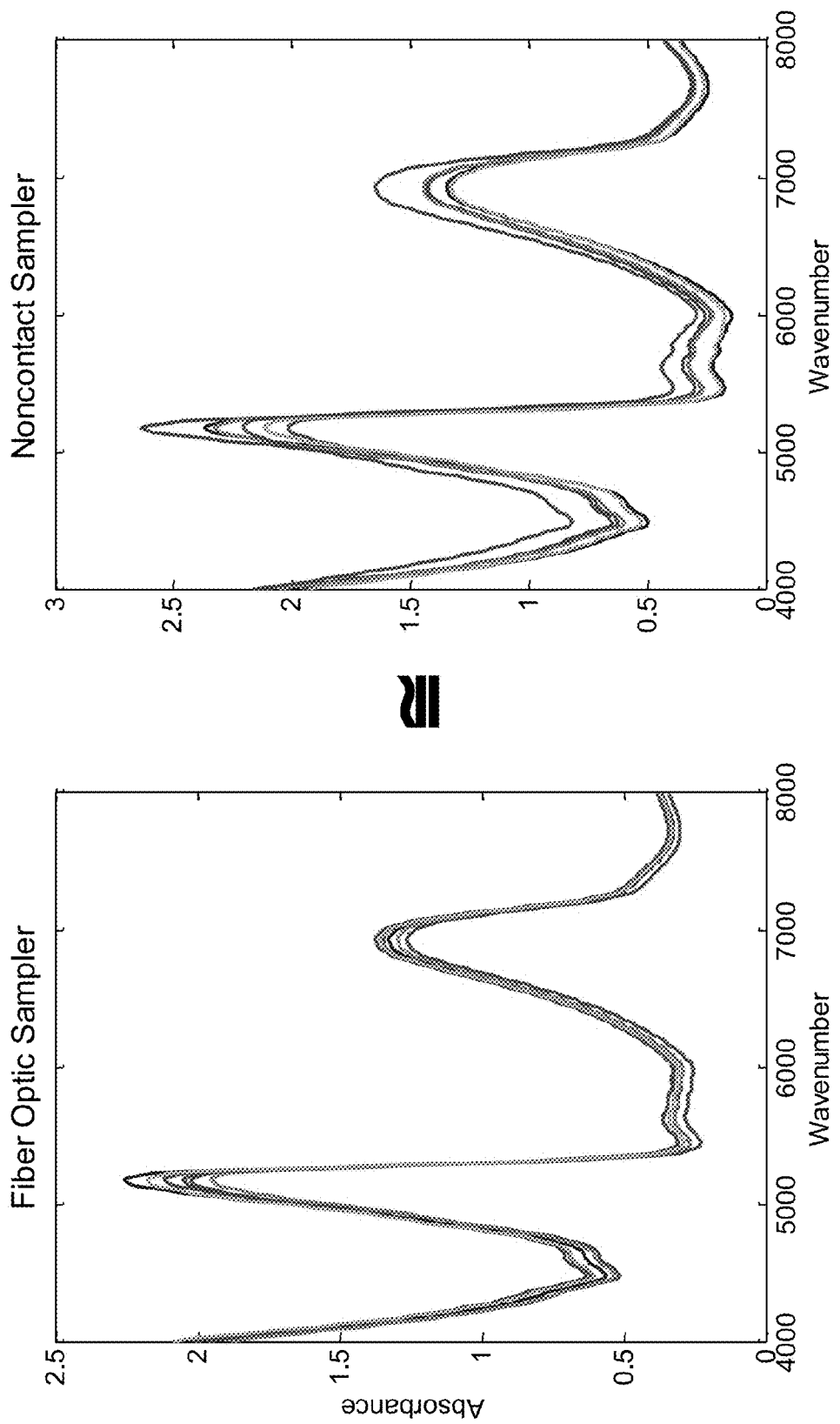
FIG. 14 is a schematic illustration of the spectral information from two optical samplers.

Spectral data were taken with both a conventional fiber optic sampler such as that shown in FIG. 13 and the system described above, operated where the illumination and collection polarizer have an amount of cross polarization of 90 degrees. A general assessment of the information content and associated optical penetration of the spectral data can be obtained by examining the height of absorbance features of the spectra; FIG. 14 shows that the two samplers provide similar spectral information.

Improved Stability During Tissue Measurement.

Figure 15:
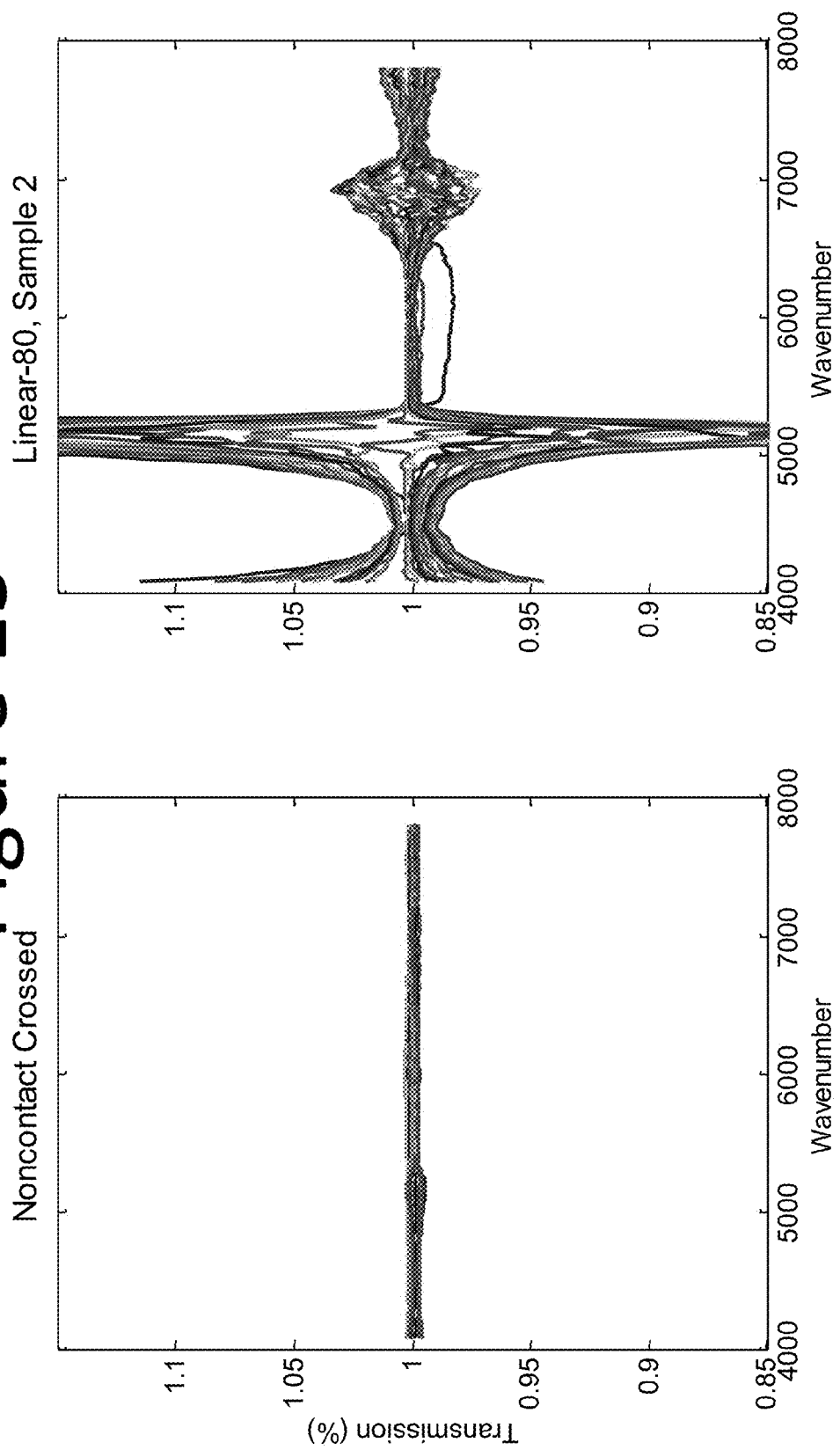
FIGS. 15 and 16 are schematic illustrations of the differences between two optical samplers in terms of measurement stability.
Figure 16:
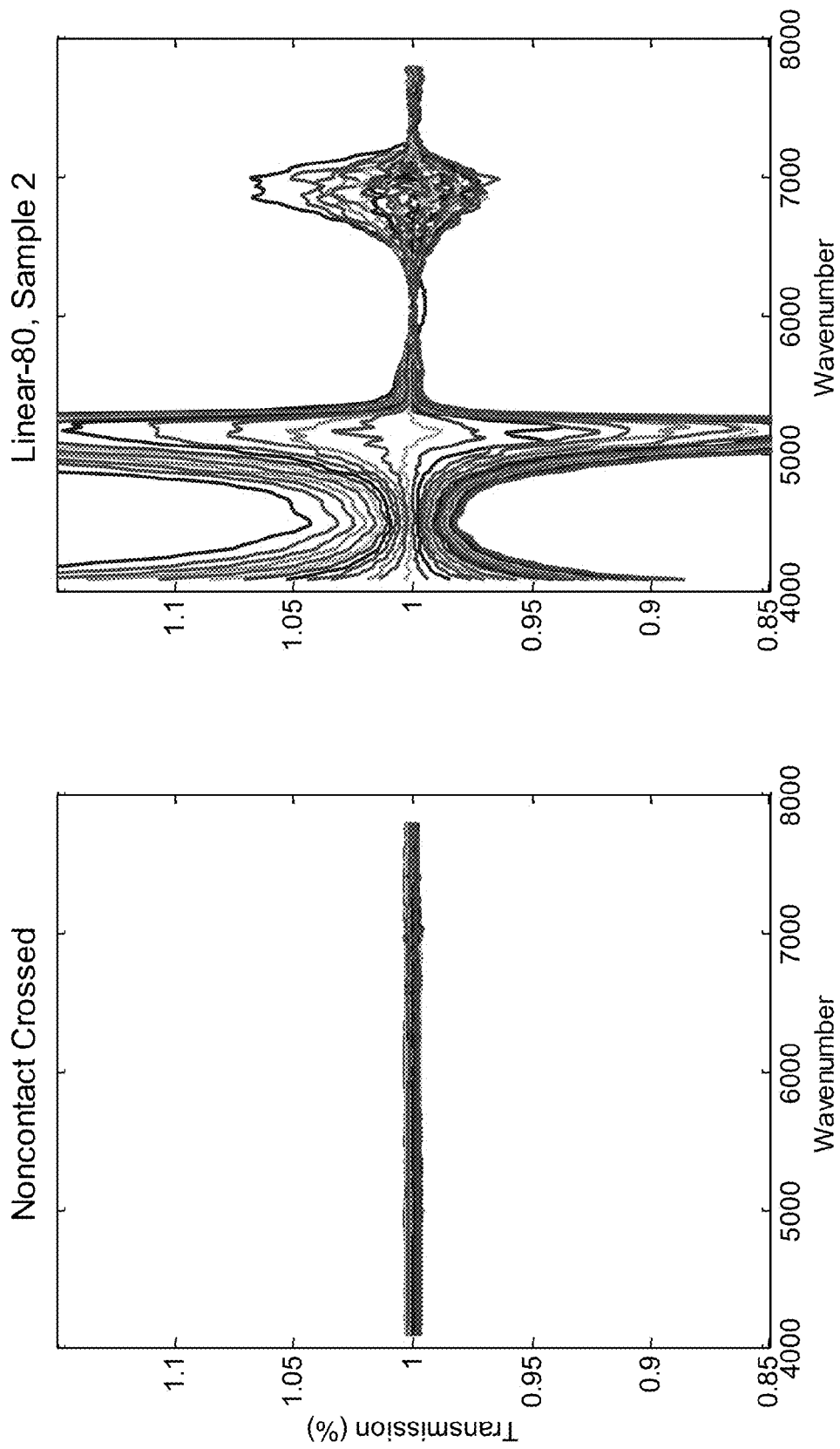

In previous samplers, contact with the tissue compresses the tissue, and the interface between the tissue and the sampler changes over the sampling period. Data from the same subjects were obtained from a conventional sampler and from the previously described non-contact sampler of FIG. 4. Data were collected for 2 minutes and mean-centered to illustrate the spectral variances that occurred during the sampling period. FIGS. 15 and 16 illustrate the differences between the two sampling systems on two subjects. The improvement can be measured by calculating the variance in pathlength. A reasonable metric for pathlength variation is to quantify the area under the water absorbance peak at 6900 cm$^{-1}$ following baseline correction. A study of 20 different individuals demonstrated an improvement of greater than 500% (i.e., reduced pathlength variation) when compared with the conventional sampler.

Demonstration that Changing Polarization Changes Pathlength in Tissue Phantoms.

Figure 17:
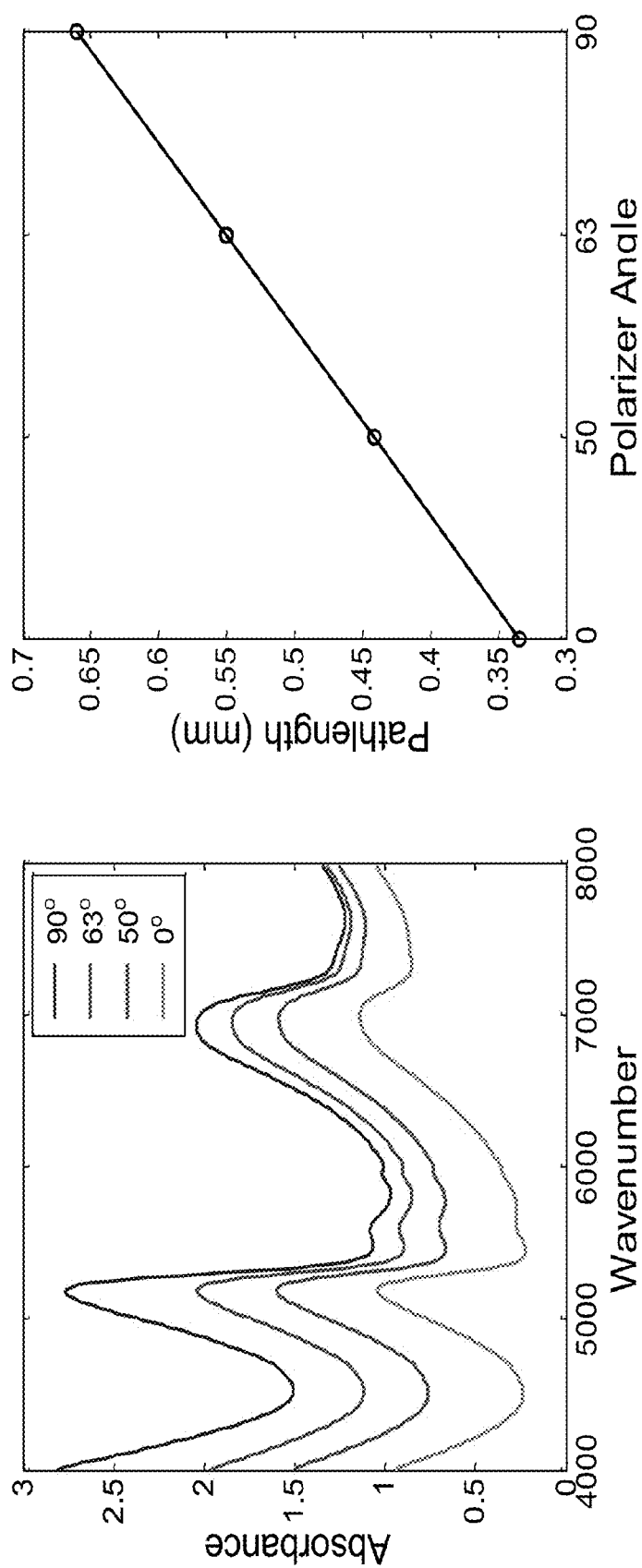
FIG. 17 is a schematic illustration of the relationship between path length and polarization angle for a single solution of scattering beads.

The length of the path over which a photon becomes depolarized depends on its initial state of polarization (linear or circular), the number of scattering events it experiences, and the scattering anisotropy of the particles it interacts with. The degree of polarization of linearly polarized light is dependent on the azimuthal angle, but circular is independent of it. The experimental system was based upon linearly polarized light, and was used to demonstrate that path length could be influenced by changing the amount of cross polarization between the illumination and collection optics. FIG. 17 shows the relationship between path length and polarization angle for a single solution of scattering beads. Four polarizer settings (0°, 50°, 63°, and 90°) were used as these polarization angles gave roughly equal changes in pathlength. The change in pathlength was quantified by calculating the area under the water absorbance peak at 6900 cm$^{-1}$ following baseline correction.

Demonstration that Changing Polarization Changes Pathlength in Tissue.

Figure 18:
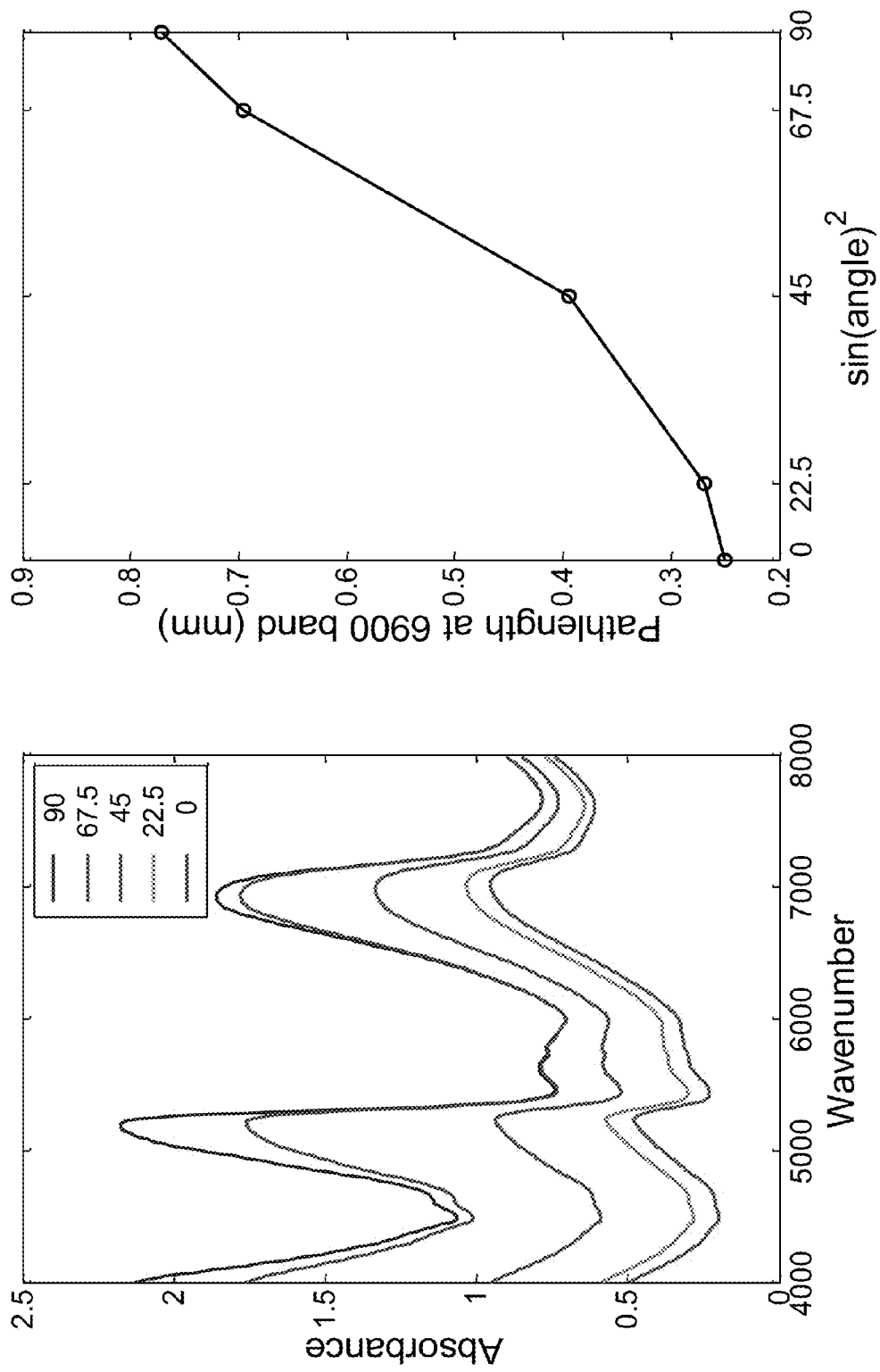
FIG. 18 is a schematic illustration of the relationship between path length and polarization angle for human tissue.

The methodology used to demonstrate pathlength variation as a function of polarization angle was repeated in human subjects. Spectral data was acquired from 5 different subjects at 0°, 22.5°, 45°, and 90°. The data were averaged together by polarization angle and the change in pathlength quantified by calculating the area under the water absorbance peak at 6900 cm$^{-1}$ following baseline correction. The resulting spectral data, presented in FIG. 18, show a increased pathlength and an increased amount of specular rejection with increasing cross polarization. The relationship between pathlength and the amount of cross polarization is shown on the right hand graph as function of sin(angle)$^2$. The resulting data shows that changing polarization can influence the optical pathlength seen in tissue spectra.

Demonstration of the Ability to Quantify Path Length Differences in Scattering Solutions.

Figure 19:
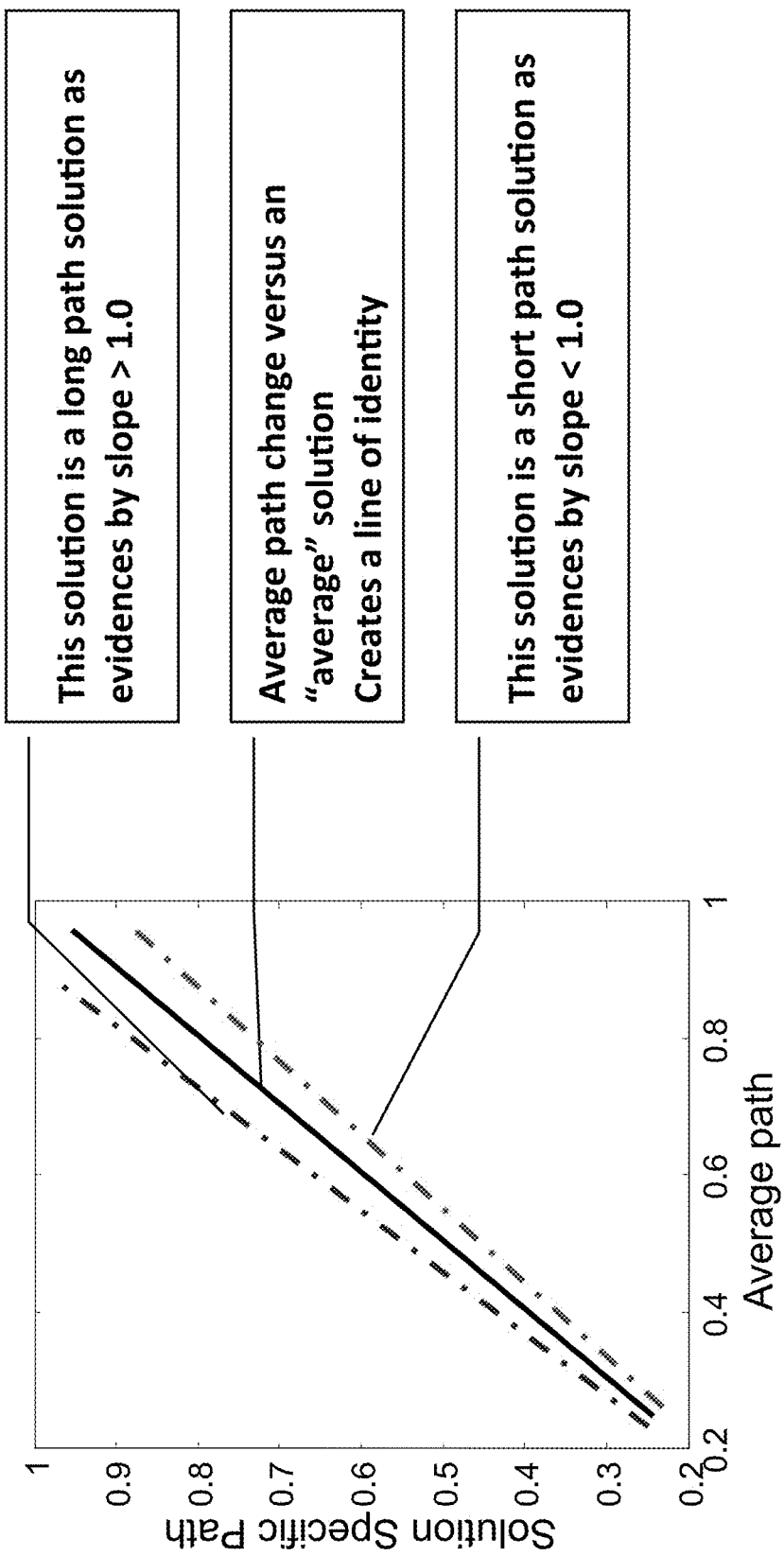
FIG. 19 is a graph explaining the relationship between measured path and average path.
Figure 20:
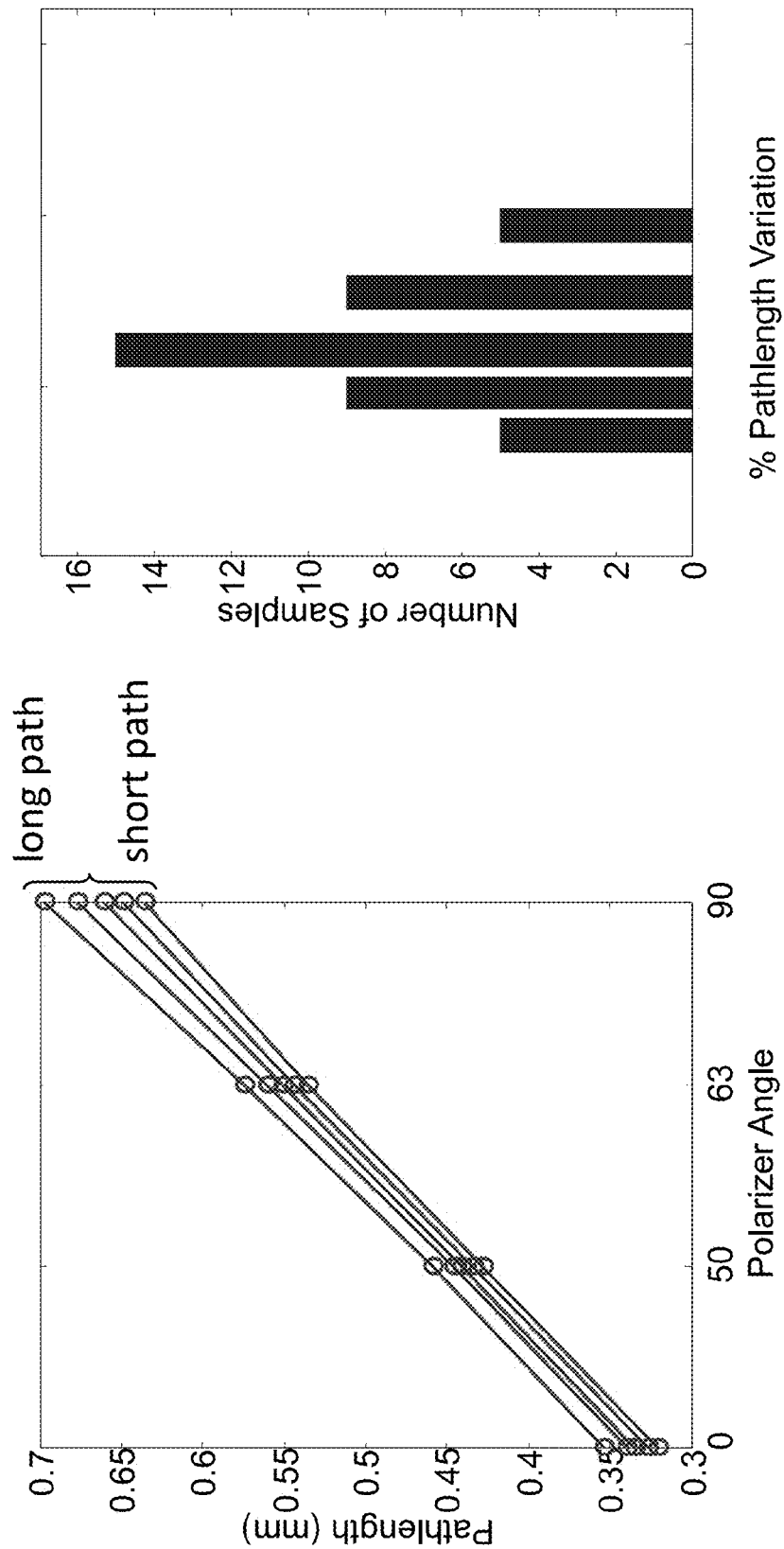
FIG. 20 is a plot of the relationship between measured path and average path for scattering solutions.

With a conventional 'monocular' sampling system, the ability to determine the scattering characteristics of a given sample is very limited. Insertion error and changes in instrument performance can make this process even more difficult. A multi-path system such as that enabled by the present invention allows the determination of relative path length. A set of variable scattering tissue phantoms were created using 9 different scattering concentrations from 4000 mg/dl to 8000 mg/dl. This variance in scatter results in a path length variation of approximately ±25%. The 9 scattering levels were sampled at four polarizer settings: 0°, 50°, 63°, 90°. The data was processed in the following manner. (1) Determine the path for each sample at each polarization angle. (2) Using all of the acquired data determine the average path as a function of polarization angle across all scattering samples. (3) Plot the determined pathlength for each solution at each different polarization angle versus the average for the solution set, as shown in FIG. 19. If the optical properties of the solution create a longer pathlength than the average, the line defined by the plot of path at each polarization will have a slope greater than one. The slope difference between the average and the observed sample defines the percentage relative difference in path length for a given sample. As seen in FIG. 20, this simple processing method can accurately characterize the tissue phantom data.

Demonstration of Path Length Variance in People.

Figure 21:
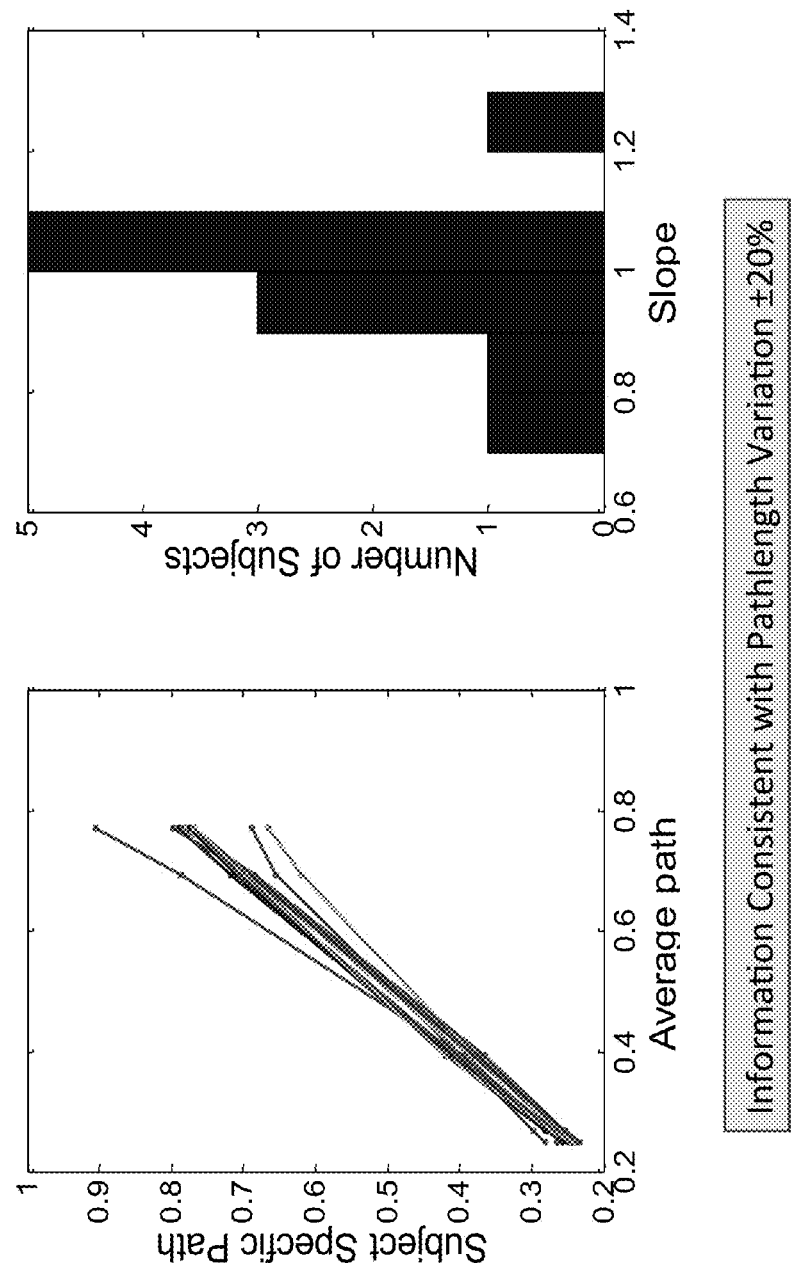
FIG. 21 is a plot of the relationship between measured path and average path for human tissue.

The method described above was used to examine the pathlength variation between human subjects. The process entailed determination of the average path as a function of angle across multiple subjects, and plotting pathlength at different polarization angles per subject versus the average path for multiple subjects. The slope difference defines the percentage (%) difference between people. As can be seen in FIG. 21, the variance in path length is approximately ±20% and the distribution appears to be Gaussian based upon our limited data set.

Adaptive Sampling Demonstrated.

For the procurement of tissue spectra that generates the most accurate glucose measurements, the optical system may change such that the desired spectral characteristic is obtained. For example, spectral data with the same or as similar as possible path length may be desirable in some applications. One method of minimizing path variation comprises defining a desired path length and then combining data from two or more different path lengths or polarizations. The method of combination is defined by the following equation:

New Spectra=$x$%*spectra 63+(1−$x$%)*spectra 90

$x$=Min(water peak$_{(Average\ specta\ 6900)}$−water peak$_{(new\ specta\ 6900)}$)

Figure 22:
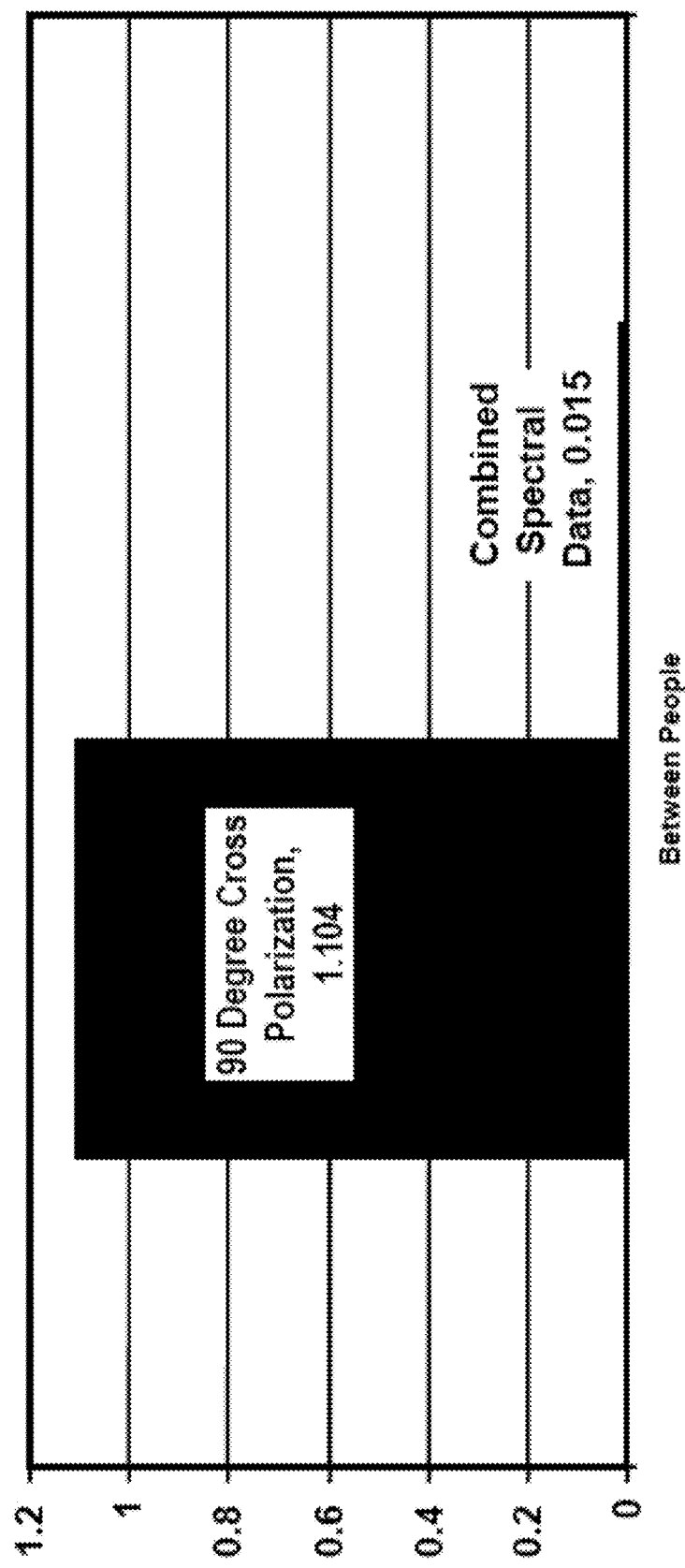
FIG. 22 is a plot demonstrating improved optical performance via adaptive sampling.

Samples from 20 different subjects at 63° and 90° cross polarizations were combined as defined by the above equation. The comparison metric was the variance under the 6900 cm$^{-1}$ band. The results plotted in FIG. 22 are for spectra data acquired at 90° cross polarization versus combined data. The results show a dramatic decrease in the calculated variance. Note that pathlength is a function of wavelength so the fitting at one point (6900 cm$^{-1}$ band) does not necessarily translate to fitting of the entire spectrum. Other methods could be employed to fit the spectrum at each wavelength, or by wavelength regions, or with a vector as a function of wavelength. The determination of the fitting coefficients can be done on de-resolved spectra and used on full resolution spectra. Additionally, the sampling system can rapidly determine the proper cross polarization and then acquire the data at only this polarization. The stability of the spectral data during the sampling period allows one to obtain data in a multitude of fashions not previously available.

Demonstration of Surface Smoothing.

Figure 23:
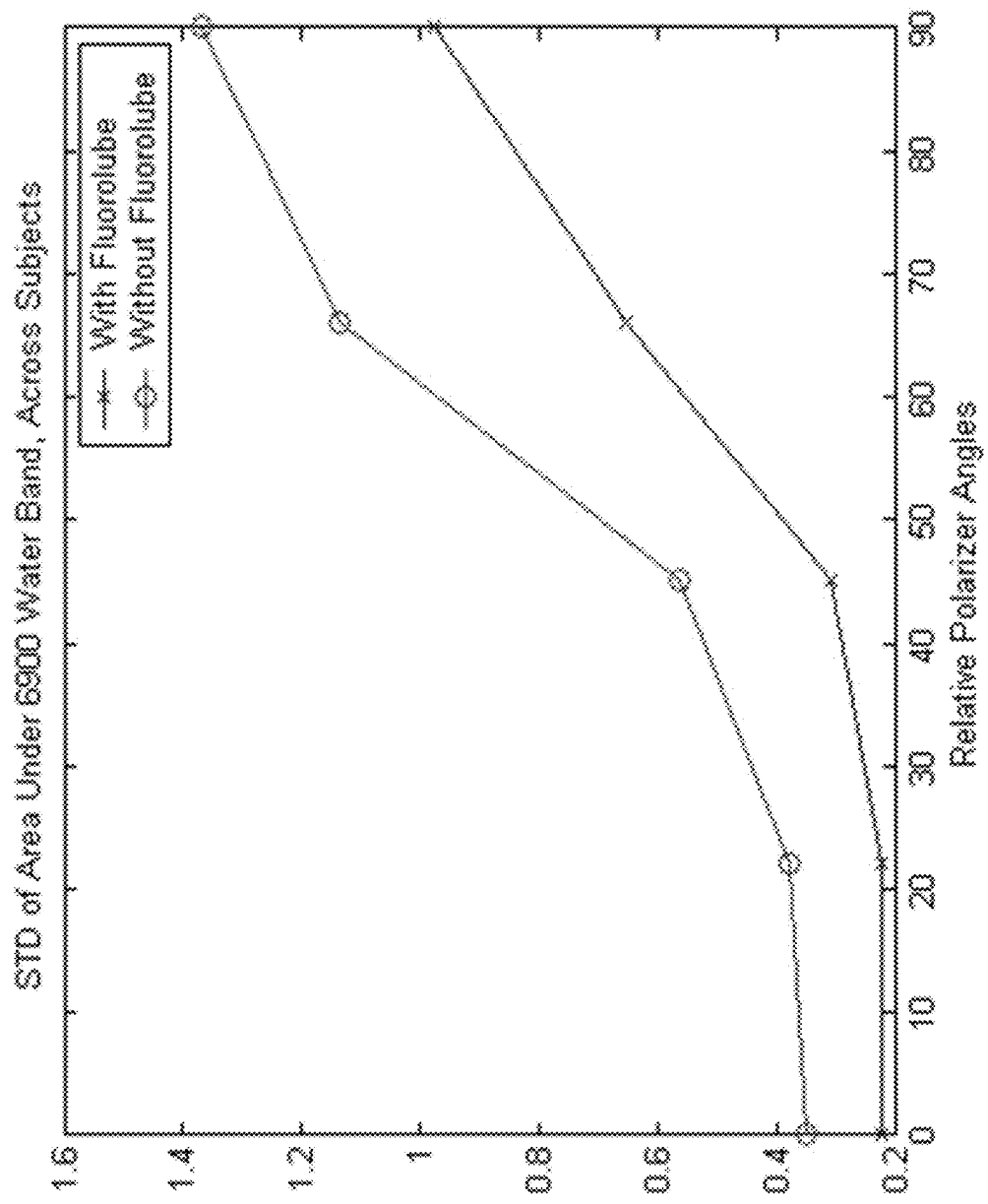
FIG. 23 is a schematic illustration showing the differences between different sampling geometries and samples.

When using polarization as a method for specular rejection, it can be desirable to have any changes in polarization occur due to within-tissue scattering events. Scattering events on the surface that change the degree of polarization can degrade the quality of the spectral data by increasing the variance in the PLD. To demonstrate the value of skin smoothing, surface oil was applied to the tissue in a non-specific manner. The oil applied was Fluorolube, a fluorinated hydrocarbon oil. This particular oil was selected as it has almost no absorbance in the region of interest. Spectral data was taken on multiple days with and without the skin smoothing oil. Examination of variance in 6900 water band at each polarization angle shows dramatic improvements; see FIG. 23. The use of a smoothing oil encouraged a smooth surface with a common refractive index and reduced tissue noise at all observed polarization angles.

Other Applications.

An individual can be identified by their spectral differences. See, e.g., U.S. Pat. Nos. 6,816,605; 6,628,809; 6,560,352; each of which is incorporated by reference herein.

Samplers according to the present invention can provide an improved biometric capability. Specifically the re-location capability and the additional information provided by multi-path sampling can improve the biometric results. Using the information available via PLD differences (either a system that changes source to detector separation or that changes polarization), one can create a biometrics identification system that can have superior performance to a system that contains information at only one PLD or depth of penetration. This information can be used like different tumblers on a combination lock: for access one must satisfy the biometrics determination at multiple layers.

As previously described, the scatter and absorbance characteristics of the tissue can impact light propagation within the tissue. In simple terms, higher absorbance contributes to shorter the pathlength, and higher scatter contributes to shorter the pathlength. These two parameters can be functions of the wavelength and are therefore not constant over the spectral region of interest. Pathlength variations can have a direct negative impact on quantitative spectroscopic measurements. Spectroscopy measures the interaction of light with a sample. In general, light intensity entering and exiting a sample is compared to extract qualitative or quantitative information. The following section outlines the assumptions inherent in spectroscopy for ideal samples before moving on to more complex systems. For illustrative purposes, this section focuses on absorbance spectroscopy in the visible and infrared regions. The visible region includes wavelengths from 380 to 780 nm. The near infrared region includes wavelengths from 780 to 2500 nm and the mid-infrared region includes wavelengths from 2500 nm to 50000 nm. This illustrative discussion is not restrictive, as the same fundamental principles apply broadly to absorption measurements outside these regions, including absorbers in the ultraviolet region and X-ray region and nuclear magnetic resonance. In the visible and infrared regions, a molecule absorbs light at frequencies characteristic of its chemical structure, which is determined by vibrational and electronic energy levels. In qualitative spectroscopy, the frequency and relative intensities of these characteristic absorbance features are used to identify specific chemical species (such as ethyl alcohol) or a broader class of chemicals (such as alcohols). In quantitative spectroscopy, the magnitude of one or more absorbance features is used to estimate the concentration of an individual chemical species in a sample (such as alcohol levels in blood) or a family of related compounds (such as total proteins in blood). Thus it is understood that the analyte measurement can estimate the concentration of a single species (such as glucose), a composite property (such as octane number of gasoline), a physical property (such as sample temperature), or a subjective sample property (such as fruit ripeness).

An idealized system for absorbance measurements is shown in FIG. 1a where the sample is presented in a cuvette with rectangular cross-section to the incident beam, which has parallel rays of monochromatic radiation. The sample transmittance (T) is the ratio of the intensity of the exiting light (I) to the incident light (Io), $$T=I/I_o$$

The sample absorbance (A) is calculated from transmission with a logarithmic transform $$A=-\log_{10}(T)=\log_{10}(I_o/I)$$

Absorbance spectra are generally used for quantitative and qualitative analysis because, in these ideal systems, their magnitude is linearly related to concentration through Beer's law:

$$A=elc$$

Where e is molar absorptivity, l is path length, and c is concentration of the absorbing species. Note that in the measurement example shown in FIG. 1a the path lengths of the three illustrated rays are equal and equivalent to the internal dimension of the cuvette. Thus path length is completely described with a scalar value of path length, l. In contrast the scattering systems shown in both a transmission (FIG. 1b) and a diffuse reflectance (FIG. 1c) measurement modes where three possible light rays are shown that have different path lengths in the sample due to scattering interactions.

Also note, that the Beer's law notation is easily extend to a spectrum measured at multiple wavelengths using a vector notation, $$A_v=e_v lc$$

where $A_v$ is a vector containing the absorbance measured at each wavelength (v), ev is a vector containing the molar absorptivity at each wavelength (v) and path length, l, is still a scalar quantities as it is the same for all wavelengths. For a measurement system with a fixed pathlength, the change in absorbance at each wavelength for a unit change in concentration will be called the pure component spectrum, Kv $$K_v=e_v l$$

The cuvette example shown in FIG. 24a and discussed in the previous section is not an accurate representation of path length changes that occur in measurements of biological samples. In these systems, the path length distribution can be different due to changes in scattering, which is defined here to broadly include interactions that change the direction of a light ray due to interactions with inhomogeneties in the sample including scattering structures described previously (such as cell structures and collagen fibers) as well as inhomogeneties from concentration gradients, temperature gradients, and diffuse reflecting surfaces (such as air-sample boundaries). FIGS. 24b and 24c show how such scattering events can change the direction of a light ray and influence its total path length within the sample. Many factors can change the scattering of a sample, including changes in the number, size, and geometry of scattering elements.

Noninvasive tissue measurements can also include significant scattering variations due, in part, to physiological variations in collagen-to-water ratios and collagen fibril diameter changes as a function of age and disease state. It should also be noted, that the very act of placing skin on an optical sampling element can change its scattering properties through compression, tension, temperature, and humidity changes.

As noted previously, the attenuation of light in tissue is described, according to light transport theory, by the effective attenuation coefficient $\mu_{eff}$, i.e.:

$$I=I_0 e^{-\mu_{eff} l}$$

Where:

$$\mu_{eff}=\sqrt{3\mu_a(\mu_a+\mu'_s)}$$

The pathlength traveled by the photons collected by the system and there corresponding PLD will be directly impacted by the $\mu_a$ and $\mu'_s$. Therefore, if these parameters can be measured or their influence measured indirectly it could be used to compensate or correct for the measurement errors due to PLD differences. Any change in the PLD between noninvasive measurements or during a noninvasive measurement can cause a change in path such that the assumptions of Beer's law are not satisfied. The net result is an error in the noninvasive measurement. Changes in the optical properties either between subjects or during a measurement cause changes in the observed PLD. Changes in the PLD can result in analyte measurement errors.

The current invention enables the measurement of spectra in both parallel ($S_{par}$) and perpendicular ($S_{per}$) polarizations states such that the degree of polarization (DOP) can be calculated. The ($S_{par}$) spectrum will contain the superficially reflected light ($R_s$) plus one half of the deeply penetrating light (Rd). The term "deeply penetrating" refers to light that has penetrated into the tissue and scattered such that the polarization state has been altered. The $S_{par}$ spectra is described as:

$$S_{par} = S_0 T_{mel}\left(R_s + \frac{1}{2}R_d\right)$$

When the analyzer is oriented perpendicular to the illumination to acquire a spectra called $S_{per}$. The $S_{per}$ spectra rejected the superficially polarized light but accepted half of the deeply penetrating light. The $S_{per}$ spectra is described $$S_{per} = S_0 T_{mel} \frac{1}{2} R_d$$

The Degree of Polarization is as follows:

$$Pol = \frac{S_{par} - S_{per}}{S_{par} + S_{per}} = \frac{S_0 T_{mel}\left(R_s + \frac{1}{2}R_d\right) - S_0 T_{mel}\frac{1}{2}R_d}{S_0 T_{mel}\left(R_s + \frac{1}{2}R_d\right) + S_0 T_{mel}\frac{1}{2}R_d} = \frac{R_s}{R_s + R_d}$$

Figure 25:
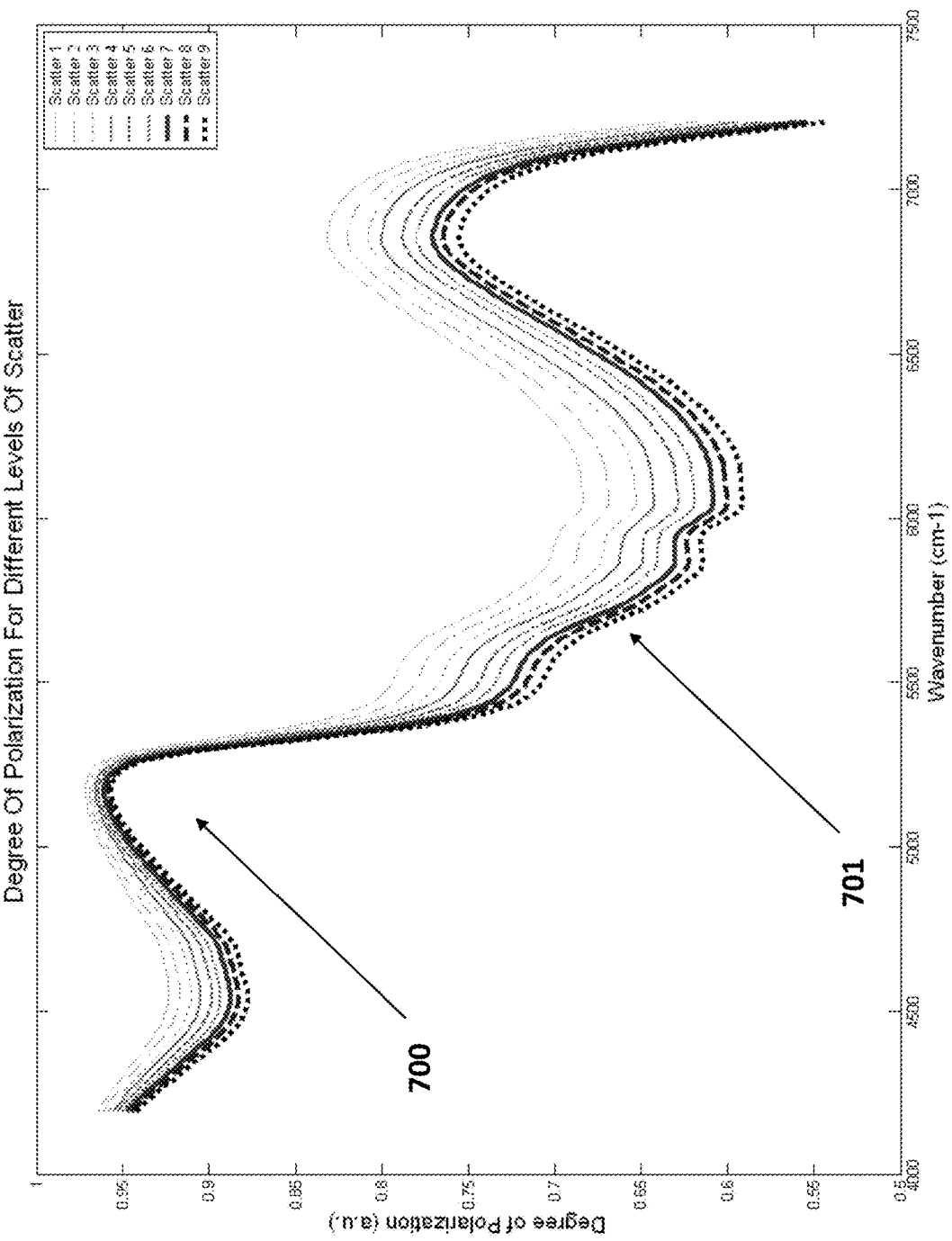
FIG. 25 is a plot of degree of polarization measurements made on human tissue.

FIG. 25 shows the DOP for a series of scattering solutions measured in a diffuse reflectance. The influence of scatter and absorbance as a function of wavelength can be readily observed. At the highly absorbing water absorbance at 5200 (cm$^{-1}$) (700) the DOP for the various scattering samples is quite similar due to the fact that absorbance is the dominant parameter in light attenuation. At shorter wavelengths (701) the influence of scatter becomes more dominant as absorbance is less significant and the DOP separation more pronounced due to scatter differences. The DOP is a measure that allows assessment of both scatter and absorbance characterizes of the sample by using the same system subsequently used for the noninvasive measurement.

The ability to make glucose, alcohol or other analyte determinations across the entire population can be limited by the differences in tissue types that cause PLD differences. These differences occur due to the way light interacts with the tissue. The key parameters of significance are scattering and absorbance. As the DOP measurement is sensitive to both parameters it can be used as a metric for compensation or identification of tissue types that have similar types of scatter and absorbance. Specifically, tissue with similar DOP will have similar PLDs. The selection of a subset of subjects with similar PLDs by use of DOP for development of calibration models and for subsequent prediction will reduce one of the largest error sources in noninvasive glucose measurements.

Figure 26:
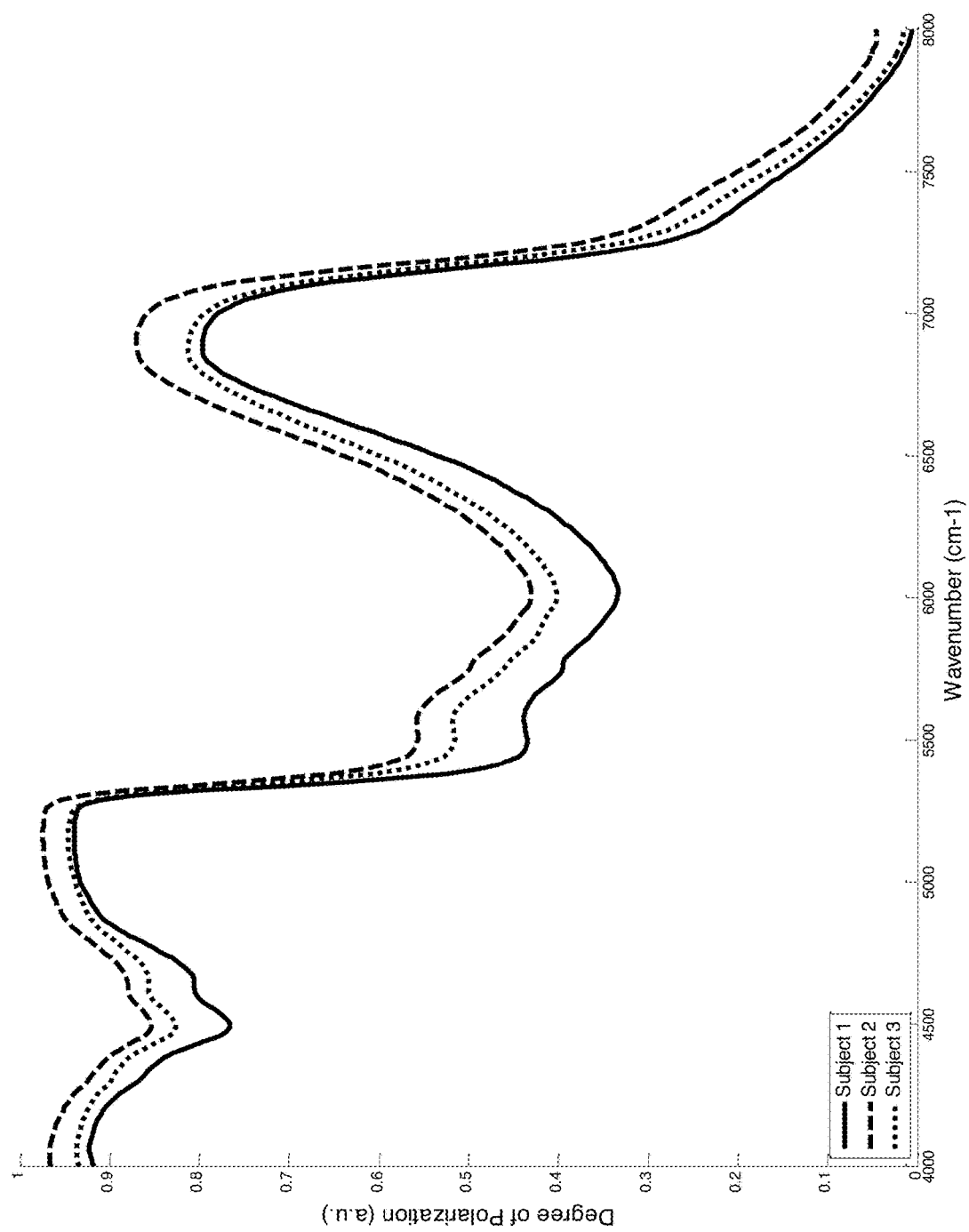
FIG. 26 shows DOP measurements for subjects taken with the system shown in FIG. 5.

FIG. 26 shows DOP measurements for subjects taken with the system shown in FIG. 5. An examination of the figure shows marked difference in the calculated DOP as a function of wavelength. The DOP differences observed are due to differences in the scatter and absorbance characteristics of the tissue being examined.

The present invention provides a system for accurate noninvasive determination of tissue properties by (1) measuring of multiple wavelengths (greater than 12) with high signal-to-noise while concurrently not burning the tissue, (2) procuring such high quality spectroscopic data in a reasonable period of time and (3) optically sampling the tissue in a repeatable manner where the tissue is not mechanically altered by the sampling process and the measured photons are preferentially selected so as to contain glucose information. In addition to these capabilities the system enables the procurement of parallel and perpendicular polarization spectra such that the degree of polarization can be calculated on the same tissue sample to be used for noninvasive analyte measurements. The DOP can subsequently be used to parameterize tissue properties and specifically to select tissue with similar PLDs. The selection of similar PLDs reduces the deviations for Beers Law behavior. Other measures of polarization or polarization characterization could be use in a manner similar to degree of polarization, such as ratio parallel and perpendicular, subtraction, etc.

The particular sizes and equipment discussed above are cited merely to illustrate particular embodiments of the invention. It is contemplated that the use of the invention may involve components having different sizes and characteristics. It is intended that the scope of the invention be defined by the claims appended hereto.

What is claimed is:

1. An apparatus for determining the presence, concentration, or both, of an analyte based upon a response of tissue to incident light, comprising:
    (a) an illumination subsystem comprising a polarizing beamsplitter configured to communicate light having a first polarization to a surface of the tissue;
    (b) a collection subsystem comprising said polarizing beamsplitter configured to collect light having a second polarization communicated from the tissue after interaction with the tissue;
    wherein the first polarization is different from the second polarization;
    (c) a multiplexing spectrometer to measure the collected light at a plurality of wavelengths;
    (d) an analysis subsystem configured to determine the presence, concentration, or both, of an analyte from the measured light.

2. An apparatus as in claim 1, wherein the first polarization is different from the second polarization such that the collection system preferentially collects light returned from deeper than the tissue surface and the superficial layer.

3. An apparatus as in claim 1, wherein the first and second polarizations are linear, with a nonzero relative angle between the first and second polarizations.

4. An apparatus as in claim 1, wherein the first and second polarizations are elliptical, and wherein the first and second polarizations are different handed.

5. An apparatus as in claim 1, wherein the multiplex spectrometer also utilizes a Jacquinot's advantage.

6. An apparatus as in claim 1, wherein the plurality of wavelengths comprises 10 or more wavelengths.

7. An apparatus as in claim 1, wherein the illumination system is configured to communicate light having any of a first plurality of polarization states to a tissue surface; or the collection system is configured to collect light having any of a second plurality of polarization states communicated from the tissue after interaction with the tissue; or both.

8. An apparatus as in claim 1, wherein at least one of the illumination system or the collection system comprises optics having a variable focus.

9. An apparatus as in claim 8, further comprising an interface quality detector, and wherein the focus of the illumination system, the focus of the collection system, or both, are varied responsive to the interface quality detector.

10. An apparatus as in claim 1, further comprising a tissue location system.

11. An apparatus as in claim 10, wherein the tissue location system comprises a system that images a component of the vascular system of a human subject whose tissue is being sampled.

12. An apparatus as in claim 10, further comprising a feedback system to communicate to a user the location of the tissue surface relative to the sampler.

13. An apparatus as in claim 10, wherein the physical relationship, relative to the tissue surface, of at least one of (a) the illumination system and (b) the collection system, can be varied responsive to the tissue location system.

14. The apparatus of claim 1 where the illumination area and the collection area are non-concentric.

15. A method of determining the presence, concentration, direction of change, rate of change, or a combination thereof, of an analyte from examination of the response of tissue to incident light, comprising:
(a) providing an apparatus as in claim 1, and
(b) applying a smoothing agent to a portion of the tissue surface;
(c) using the apparatus, illuminating the portion of the tissue surface such that illumination light impinges on the smoothing agent before impinging on the tissue surface, and collecting light communicated from the tissue surface without physically contacting the smoothing agent with the optical sampler, and determining the presence, concentration, or both, of the analyte from the measured light.

16. A method as in claim 15, further comprising analyzing the light measurements from the multiplexing spectrometer to determine the presence of the smoothing agent.

17. A method as in claim 16, wherein the smoothing agent has a characteristic absorption, and wherein analyzing the light measurements comprises determining whether the collected light has interacted with a material having the characteristic absorption.

18. A method as in claim 17, further comprising determining a thickness of smoothing agent that has interacted with the light from the light measurements.

19. An apparatus as in claim 1, wherein the illumination subsystem and the collection subsystem are configured to collect spectroscopic information at a first polarization state and at a second polarization state, where the first and second polarization states are distinct, and wherein the multiplexing spectrometer utilizes multiplex advantage, and wherein the analysis subsystem is configured to use at least a portion of the information obtained at each of the two polarization states.

20. An analyte measurement system as in claim 19 where the analysis subsystem is configured to use the information from the two polarization states to characterize tissue differences.

21. An analyte measurement system as in claim 20, where the information obtained from the two polarization states is used to calculate the degree of polarization.

22. An analyte measurement system as in claim 20 where the analysis subsystem is configured to select a measurement method responsive at least in part to the tissue differences.

23. A method of determining the response of portions of a tissue sample deeper than the superficial layer to light, comprising
(a) providing an apparatus as in claim 1, wherein the collection subsystem is further configured to collect light having a third polarization communicated from the tissue after interaction with the tissue; and:
(b) using the illumination subsystem to illuminate the tissue sample with light having a first polarization;
(c) using the collection system to collect light, in a non-imaging manner, having a second polarization;
(d) using the collection system to collect light, in a non-imaging manner, having a third polarization to preferentially select photons from tissue deeper than the superficial layer;
(e) wherein the second polarization, and the third polarization are each different from one another; and
(f) measuring the collected light at a plurality of wavelengths using the multiplexing spectrometer.

24. A method as in claim 23, wherein the first, second, and third polarizations are linear.

25. A method as in claim 23, wherein the first, second, and third polarizations are elliptical, and wherein the second and third polarizations are different handed.

26. A method as in claim 23, wherein the tissue is illuminated and light collected from substantially the same tissue portion at each of the first, second, and third polarizations.

27. A method as in claim 23, further comprising determining the presence or concentration of an analyte from the measured light in step (f).

28. An apparatus as in claim 1, wherein the analyte is glucose, and wherein the analysis system is configured to determine a glucose concentration from multivariate analysis of at least 10 wavelengths of light.

* * * * *